United States Patent [19]

Yamada et al.

[11] Patent Number: 5,356,558
[45] Date of Patent: Oct. 18, 1994

[54] TOLANE DERIVATIVES, LIQUID CRYSTAL COMPOSITIONS CONTAINING THE DERIVATIVES AND LIQUID CRYSTAL DISPLAY DEVICES USING THE COMPOSITIONS

[75] Inventors: Shuhei Yamada; Shuji Ikukawa; Jun Ito; Jitsuko Nakayama, all of Suwa, Japan

[73] Assignee: Seiko Epson Corporation, Tokyo, Japan

[21] Appl. No.: 94,353

[22] Filed: Jul. 21, 1993

[30] Foreign Application Priority Data

| Jul. 28, 1992 | [JP] | Japan | 4-201333 |
| Sep. 18, 1992 | [JP] | Japan | 4-250006 |
| Jan. 8, 1993 | [JP] | Japan | 5-001933 |
| Mar. 10, 1993 | [JP] | Japan | 5-049571 |
| May 24, 1993 | [JP] | Japan | 5-121701 |

[51] Int. Cl.$^5$ .................. C09K 19/52; C07C 255/50; C07C 25/24; G02F 1/13
[52] U.S. Cl. .................. 252/299.01; 252/299.61; 252/299.63; 252/299.67; 558/411; 558/425; 570/127; 359/103
[58] Field of Search .................. 252/299.01, 299.61, 252/299.63, 299.64, 299.66, 299.67; 359/103; 558/411, 425; 570/127

[56] References Cited

FOREIGN PATENT DOCUMENTS 0345013 12/1989 European Pat. Off. .
4005882 8/1991 Fed. Rep. of Germany .
1-305040 12/1989 Japan .

OTHER PUBLICATIONS

Chemical Abstracts, vol. 95, Dec. 21, 1981, Abstract No. 219871, p. 494.
P. Adomenas et al., "Acetylenic Liquid Crystals Available by Castro Reaction", *Advances in Liquid Crystal Research and Applications*, 1980, pp. 1029–1038.

*Primary Examiner*—Shean Wu
*Attorney, Agent, or Firm*—Oliff & Berridge

[57] ABSTRACT

A tolane derivative, a liquid crystal composition containing the derivative, and a liquid crystal display device including the composition, in which the tolane derivative is represented by the following general formula:

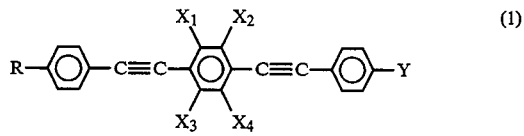

wherein R represents a straight-chain alkyl group having 1 to 10 carbon atoms, and each of $X_1$, $X_2$, $X_3$ and $X_4$ represents a fluorine atom or a hydrogen atom wherein at least one X represents a fluorine atom, and Y represents a nitrile group or a straight-chain alkyl group having 1 to 10 carbon atoms.

By blending the above-described compound with a general liquid crystal composition, a liquid crystal composition is provided which exhibits a wide practical temperature range as well as a large anisotropy of refractive index.

12 Claims, 1 Drawing Sheet

TOLANE DERIVATIVES, LIQUID CRYSTAL COMPOSITIONS CONTAINING THE DERIVATIVES AND LIQUID CRYSTAL DISPLAY DEVICES USING THE COMPOSITIONS

BACKGROUND OF THE INVENTION

1. Field of the Invention

The present invention relates to a novel tolane derivative used as a component of electro-optic display materials, a liquid crystal composition containing the derivative and a liquid crystal display device using the composition.

2. Description of the Prior Art

Liquid crystal display devices utilize the electro-optical effect of the liquid crystal. The display modes currently used include the twisted nematic (hereinafter referred to as TN) mode and the super twisted nematic (hereinafter referred to as STN) mode which has a larger twist angle. The characteristics required for these display modes are as follows:

1. Colorless and thermal-, photo-, electrical- and chemical stabilities;
2. Wide practical temperature range;
3. Electro-optical high-speed response;
4. Low driving voltage;
5. Rapid rising of voltage-light transmittance characteristic, and small temperature dependency of the threshold voltage (hereinafter referred to as Vth); and
6. Wide visual angle.

A number of liquid crystal compounds which satisfy characteristic 1 are well known. However, no single liquid crystal compound is known which satisfies characteristics 2-6. Therefore, in order to satisfy these characteristics, liquid crystal compositions in which several kinds of nematic liquid crystal compounds or nonliquid crystal compounds are blended have been used.

For example, in order to satisfy characteristic 2, a liquid crystal compound is required which has not only a low crystal phase-nematic liquid crystal phase transition point (hereinafter referred to as C-N point) but also a high nematic liquid crystal phase-isotropic liquid transition point (hereinafter referred to as N-I point) and consequently a wide temperature range of nematic liquid crystal phase.

On the other hand, in order to satisfy characteristic 3, i.e., to make the response speed fast, the cell gap should be decreased in the relation between the response speed (hereinafter referred to as $\tau$), the viscosity coefficient (hereinafter referred to as n) and the cell gap (hereinafter referred to as d) represented by the following equation:

$$\tau \propto nd^2$$

In the cell practically used, in order to prevent the occurrence of interference fringes on the surface of the cell which causes damage to the cell appearance, the $\Delta n \cdot d$ is adjusted to a constant value. $\Delta n$ means the anisotropy of refractive index; the same applies to the other $\Delta n$ hereinafter. Therefore, by using a material having a high $\Delta n$ value, the d value can be made small and, consequently, the response speed can be increased.

In order to satisfy characteristics 2 and 3 simultaneously, there are known tolane derivatives which are described in Adv. in Liquid Crystal Research and Application (edited by L. Bata), Oxford: Pergamon Press; Budapest: Akademiai Kiado 1980, S. 1029; Japanese Patent Application Laid-Open No. 305040/1989; and so on, as liquid crystal materials having not only a wide temperature range of nematic liquid crystal phase but also a large $\Delta n$ value.

TABLE 1

| No. | Structural Formula | Transition Point | Literature |
|---|---|---|---|
| (i) | $C_5H_{11}$—⌬—C≡C—⌬(Cl)—C≡C—⌬—$C_5H_{11}$ | C-N point: 100° C.<br>N-I point: 194° C. | Adv. in Liquid Crystal Research and Application. |
| (ii) | $C_5H_{11}$—⌬—C≡C—⌬(CN)—C≡C—⌬—$C_5H_{11}$ | C-N point: 77° C.<br>N-I point: 152° C. | Adv. in Liquid Crystal Research and Application. |
| (iii) | $C_3H_7$—⌬—C≡C—⌬—C≡C—⌬—$C_3H_7$ | C-N point: 179° C.<br>N-I point: 246° C. | Japanese Patent Application Laid-open No. 305040/1989 |
| (iv) | $C_4H_9$—⌬—C≡C—⌬—C≡C—⌬—$C_4H_9$ | C-N point: 152° C.<br>N-I point: 216° C. | Japanese Patent Application Laid-open No. 305040/1989 |

TABLE 1-continued

| No. | Structural Formula | Transition Point | Literature |
|---|---|---|---|
| (v) | C$_5$H$_{11}$—⟨○⟩—C≡C—⟨○⟩—C≡C—⟨○⟩—C$_5$H$_{11}$ | C–N point: 151° C. N–I point: 212° C. | Japanese Patent Application Laid-open No. 305040/1989 |

It is described in the above literature that compounds (i) and (ii) have a nematic state in a wide temperature range and have no smectic state, and that compounds (iii), (iv) and (v) have well-balanced desirable properties as liquid crystal components such as an extremely large Δn value, a low viscosity for compounds of three-ring structure and a high N-I point, respectively.

However, in compounds (i) and (ii), the Δn is expected to become smaller, since they have a chloride group or nitrile group in the side chains of their skeletons. On the other hand, compounds (iii), (iv) and (v) have C-N points of 150° C. or higher, and consequently it appears that the compounds have poor compatability with other liquid crystal compounds.

SUMMARY OF THE INVENTION

The present invention solves the problems mentioned above. It is an object of the present invention to provide a novel liquid crystal compound which exhibits excellent compatibility with several kinds of nematic liquid crystal compounds or non-liquid crystal compounds, and from which a novel liquid crystal composition, having a wide practical temperature range and a large Δn value, can be obtained by blending with the compound.

Another object of the present invention is to provide a liquid crystal display device having a wide practical temperature range and a high-speed response.

The present invention provides a tolane derivative, a liquid crystal composition containing the derivative and a liquid crystal display device using the composition. The tolane derivative is represented by the following general formula:

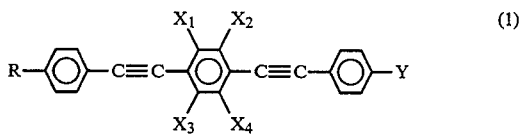

wherein R represents a straight-chain alkyl group having 1 to 10 carbon atoms, each of $X_1$, $X_2$, $X_3$ and $X_4$ represents a fluorine atom or a hydrogen atom wherein at least one X represents a fluorine atom, and Y represents a nitrile group or a straight-chain alkyl group having 1 to 10 carbon atoms.

DETAILED DESCRIPTION OF THE INVENTION

Figure 1:
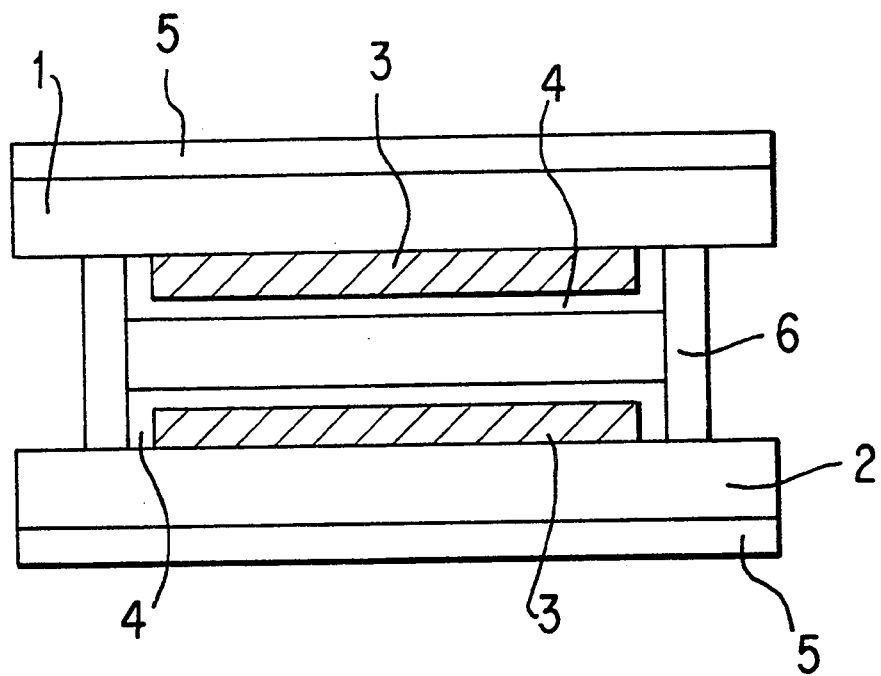
FIG. 1 illustrates the liquid crystal display cell produced according to the present invention.

Compound (1) of the present invention can be prepared according to the following reaction steps:

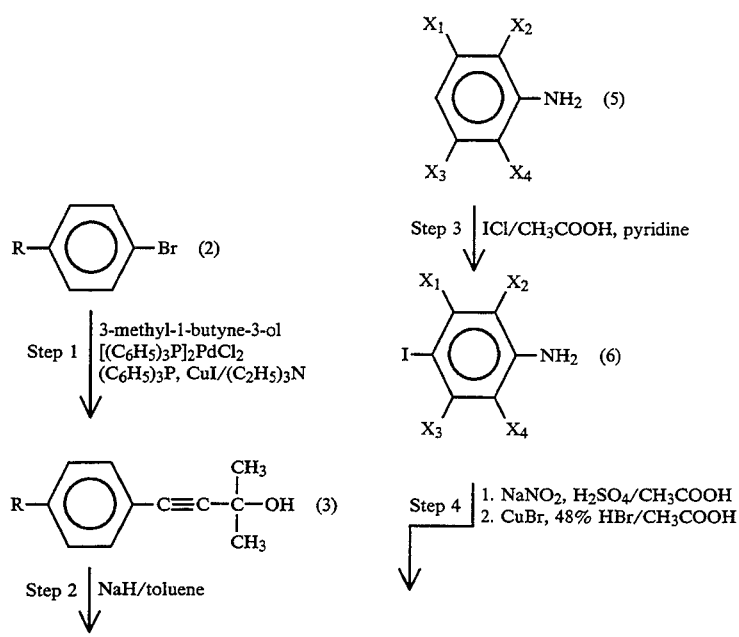

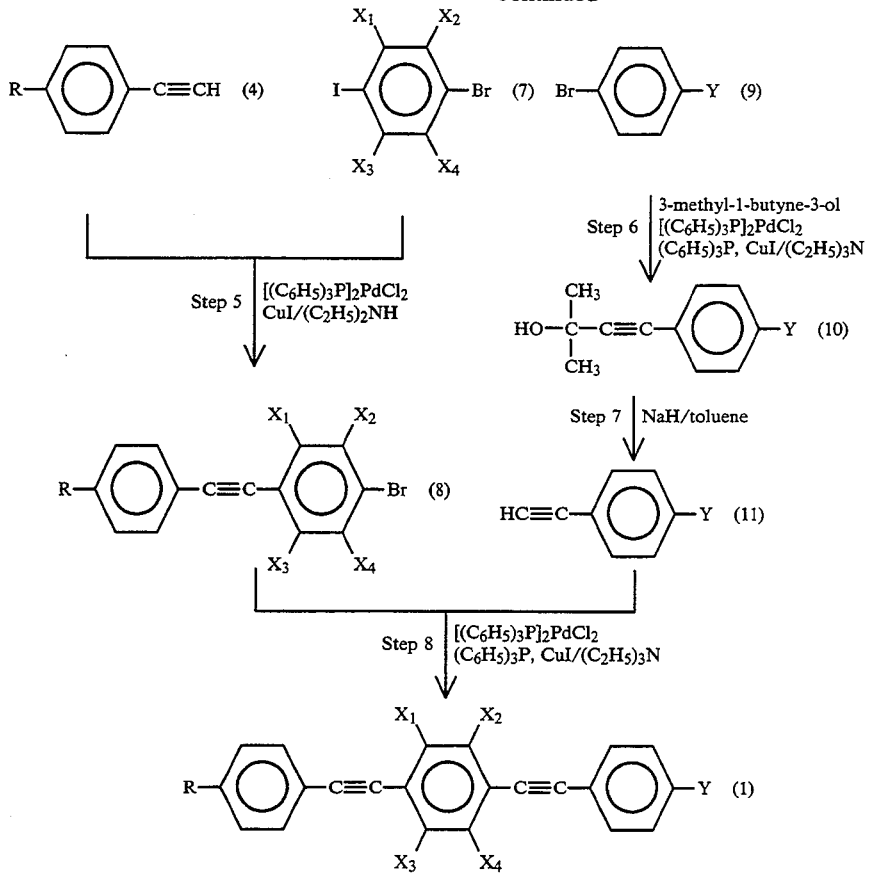

In the above formulae, R represents a straight-chain alkyl group having 1 to 10 carbon atoms, each of $X_1$, $X_2$, $X_3$ and $X_4$ represents a fluorine atom or a hydrogen atom wherein at least one X represents a fluorine atom, and Y represents a nitrile group or a straight-chain alkyl group having 1 to 10 carbon atoms.

Step 1: Compound (2) is reacted with 3-methyl-1-butyne-3-ol in triethylamine in the presence of bis(triphenylphosphine)palladium(II) chloride, triphenylphosphine and copper(I) iodide to give Compound (3).

Step 2: Compound (3) is reacted with sodium hydride in toluene to give Compound (4).

Step 3: Compound (5) is reacted with iodine monochloride in acetic acid in the presence of pyridine to give Compound (6).

Step 4: Compound (6) is reacted with sodium nitrite and sulfuric acid in acetic acid to be converted into a diazonium salt, followed by reaction with copper(I) bromide and hydrobromic acid, to give Compound (7). In the case where Compound (6) is commercially available, however, Step 3 is not needed, and where Compound (7) is commercially available, Steps 3 and 4 are not needed.

Step 5: Compound (4) is reacted with Compound (7) in diethylamine in the presence of bis(triphenylphosphine)palladium(II) chloride and copper(I) iodide to give Compound (8).

Step 6: Compound (9) is reacted with 3-methyl-1-butyne-3-ol in triethylamine in the presence of bis(triphenylphosphine)palladium(II) chloride, triphenylphosphine and copper(I) iodide to give Compound (10).

Step 7: Compound (10) is reacted with sodium hydride in toluene to give Compound (11).

Step 8: Compound (8) is reacted with Compound (11) in triethylamine in the presence of bis(triphenylphosphine)palladium(II) chloride, triphenylphosphine and copper(I) iodide to give Compound (1).

Examples of base components of the liquid crystal composition to be mixed with the tolane derivatives of the present invention are shown below, but are not limited thereto. The tolane derivatives of the present invention exhibit excellent compatibility with all conventional liquid crystal compounds or their analogues. The resulting liquid crystal compositions have wide practical temperature ranges and large Δn values.

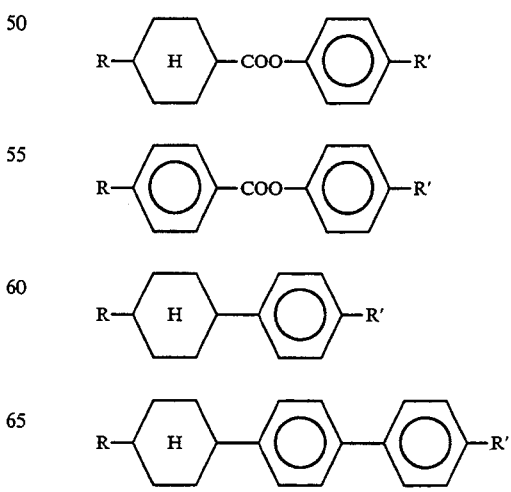

-continued

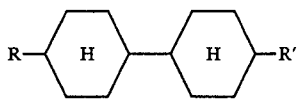

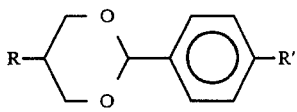

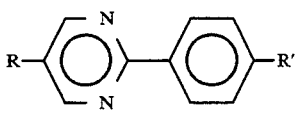

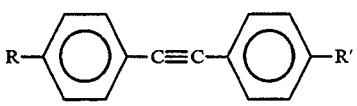

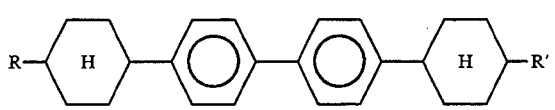

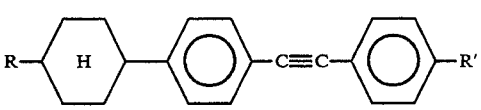

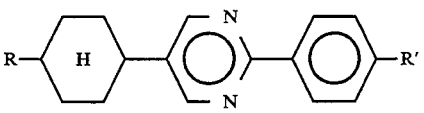

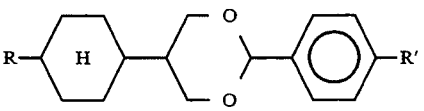

In the above formulae, each of R and R' represents an alkyl group, an alkoxy group, an alkoxymethylene group, a nitrile group or a fluoro group. The phenylene group may have a halogen substituent at the 2-position or 3-position; and the cyclohexane ring is trans configuration.

The blending ratio of the compounds of the present invention in a liquid crystal composition is in the range of 1 to 50 wt %. It is particularly preferred to be in the range of 3 to 30 wt % considering the precipitation of the crystals in the low temperature region.

A liquid crystal display apparatus using a liquid crystal composition containing at least one of the compounds of the invention is highly suitable for a liquid crystal display apparatus which utilizes a time-sharing addressing mode. In particular, TN mode- and STN mode-liquid crystal display devices prepared with the inventive compositions can be driven by high time-sharing addressing.

EXAMPLES

To further illustrate the present invention, the following examples will be given.

EXAMPLE 1:

Synthesis of Compound (1-a)

Preparation of 1-(4'-propylphenylethynyl)-4-(4"-pentylphenylethynyl)-2-fluorobenzene.

Step 1: 1-Bromo-4-propylbenzene (60 g), 3-methyl-1-butyne-3-ol (38 g), triphenylphosphine (1.3 g) and bis(triphenylphosphine)palladium(II) chloride (0.7 g) were dissolved in triethylamine (260 ml) under nitrogen atmosphere, and then copper(I) iodide (0.2 g) was added thereto. The mixture was stirred at room temperature for 1 hour, and then further stirred at 90° C. for 5 hours. The resulting precipitated crystals were filtered, and then triethylamine was distilled off, followed by extraction with chloroform. The resultant was washed twice with 10% hydrochloric acid, and further with water twice, followed by distilling off chloroform therefrom. The residue was purified by the use of silica gel-chloroform column chromatography to give 3-methyl-1-(4'-propylphenyl)-1-butyne-3-ol (37 g).

Step 2: 3-Methyl-1-(4'-propylphenyl)-1-butyne-3-ol (33 g) was dissolved in toluene (320 ml) under nitrogen atmosphere, and then sodium hydride (60% in 2 g of paraffin liquid) was added thereto. The mixture was stirred at 60° C. for 6 hours. The reaction solution was poured into water (300 ml), and then extracted with chloroform, followed by washing with water three times. After distilling off toluene and chloroform, the resultant was distilled under reduced pressure (b.p. 60° to 63° C./4 mmHg) to give 4-propylphenylacetylene (16 g).

Steps 3 and 4: These steps were not needed to be carried out, since 4-bromo-2-fluoro-1-iodobenzene is commercially available.

Step 5: 4-Bromo-2-fluoro-1-iodobenzene (33 g) was dissolved in diethylamine (37 ml) under nitrogen atmosphere, and then bis(triphenylphosphine)palladium(II) chloride (0.1 g) and copper(I) iodide (0.1 g) were added thereto, followed by stirring. The flask was cooled to 5° C. or lower, and then 4-propylphenylacetylene (16 g) was added dropwise thereto. After stirring at room temperature for 5 hours, the reaction solution was poured into a mixture of concentrated hydrochloric acid (23 ml) and ice (150 g). After extraction with chloroform, the resultant was washed twice with water, followed by distilling off chloroform therefrom. The residue was distilled under reduced pressure (b.p. 190° to 200° C./4 mmHg), and then recrystallized from a mixed solvent of acetone and methanol to give 4-bromo-2-fluoro-4'-propyltolane (23 g).

Step 6: 1-Bromo-4-pentylbenzene (102 g), 3-methyl-1-butyne-3-ol (38 g), triphenylphosphine (2 g) and bis(triphenylphosphine)palladium(II) chloride (1 g) were dissolved in triethylamine (390 ml) under nitrogen atmosphere, and then copper(I) iodide (0.3 g) was added thereto. After stirring at room temperature for 1 hour, the reaction mixture was further stirred at 90° C. for 5 hours. The resulting precipitated crystals were filtered, and then triethylamine was distilled off therefrom, followed by extracting with chloroform. The resultant was washed twice with 10% hydrochloric acid, and further with water twice, and then chloroform was distilled off therefrom. The residue was purified using silica gel-chloroform column chromatography to give 3-methyl-1-(4'-pentylphenyl)-1-butyne-3-ol (82 g).

Step 7: 3-Methyl-1-(4'-pentylphenyl)-1-butyne-3-ol (82 g) was dissolved in toluene (900 ml) under nitrogen atmosphere, and then sodium hydride (60% in paraffin liquid; 5.6 g) was added thereto, followed by stirring at 60° C. for 6 hours. The reaction solution was poured into water (500 ml), and extracted with chloroform, followed by washing with water three times. After distilling off toluene and chloroform, the resultant was distilled under reduced pressure (b.p. 85° to 90° C./3 mmHg) to give 4-pentylphenylacetylene (48 g).

Step 8: 4-Bromo-2-fluoro-4'-propyltolane (3.8 g), 4-pentylphenylacetylene (2.1 g), triphenylphosphine (0.05 g) and bis(triphenylphosphine)palladium(II) chloride (0.02 g) were dissolved in triethylamine (27 ml) under nitrogen atmosphere, and then copper(I) iodide (0.01 g) was added thereto, followed by refluxing for 5 hours. The reaction solution was poured into water (300 ml), and then extracted with chloroform. After washing the resultant with water twice, chloroform was distilled off therefrom. The residue was purified using silica gel-chloroform column chromatography, and then recrystallized from acetone to give 1-(4'-propylphenylethynyl)-4-(4''-pentylphenylethynyl)-2-fluorobenzene (1.4 g). The C-N point and the N-I point of the compound were 81.3° C. and 202.7° C., respectively.

The following compounds were synthesized in the same manner as the above method:
1,4-bis(4'-methylphenylethynyl)-2-fluorobenzene
1-(4'-methylphenylethynyl)-4-(4''-ethylphenylethynyl)-2-fluorobenzene
1-(4'-methylphenylethynyl)-4-(4''-propylphenylethynyl)-2-fluorobenzene
1-(4'-methylphenylethynyl)-4-(4''-butylphenylethynyl)-2-fluorobenzene
1-(4'-methylphenylethynyl)-4-(4''-pentylphenylethynyl)-2-fluorobenzene
1-(4'-methylphenylethynyl)-4-(4''-hexylphenylethynyl)-2-fluorobenzene
1-(4'-methylphenylethynyl)-4-(4''-heptylphenylethynyl)-2-fluorobenzene
1-(4'-methylphenylethynyl)-4-(4''-octylphenylethynyl)-2-fluorobenzene
1-(4'-methylphenylethynyl)-4-(4''-nonylphenylethynyl)-2-fluorobenzene
1-(4'-methylphenylethynyl)-4-(4''-decylphenylethynyl)-2-fluorobenzene
1-(4'-ethylphenylethynyl)-4-(4''-methylphenylethynyl)-2-fluorobenzene
1,4-bis(4'-ethylphenylethynyl)-2-fluorobenzene
1-(4'-ethylphenylethynyl)-4-(4''-propylphenylethynyl)-2-fluorobenzene
1-(4'-ethylphenylethynyl)-4-(4''-butylphenylethynyl)-2-fluorobenzene
1-(4'-ethylphenylethynyl)-4-(4''-pentylphenylethynyl)-2-fluorobenzene
1-(4'-ethylphenylethynyl)-4-(4''-hexylphenylethynyl)-2-fluorobenzene
1-(4'-ethylphenylethynyl)-4-(4''-heptylphenylethynyl)-2-fluorobenzene
1-(4'-ethylphenylethynyl)-4-(4''-octylphenylethynyl)-2-fluorobenzene
1-(4'-ethylphenylethynyl)-4-(4''-nonylphenylethynyl)-2-fluorobenzene
1-(4'-ethylphenylethynyl)-4-(4''-decylphenylethynyl)-2-fluorobenzene
1-(4'-propylphenylethynyl)-4-(4''-methylphenylethynyl)-2-fluorobenzene
1-(4'-propylphenylethynyl)-4-(4''-ethylphenylethynyl)-2-fluorobenzene
C-N point 150.3° C., N-I point 214.1° C.
1,4-bis(4'-propylphenylethynyl)-2-fluorobenzene
C-N point 147.0° C., N-I point 220.0° C.
1-(4'-propylphenylethynyl)-4-(4''-butylphenylethynyl)-2-fluorobenzene
C-N point 112.4° C., N-I point 203.7° C.
1-(4'-propylphenylethynyl)-4-(4''-hexylphenylethynyl)-2-fluorobenzene
1-(4'-propylphenylethynyl)-4-(4''-heptylphenylethynyl)-2-fluorobenzene
1-(4'-propylphenylethynyl)-4-(4''-octylphenylethynyl)-2-fluorobenzene
1-(4'-propylphenylethynyl)-4-(4''-nonylphenylethynyl)-2-fluorobenzene
1-(4'-propylphenylethynyl)-4-(4''-decylphenylethynyl)-2-fluorobenzene
1-(4'-butylphenylethynyl)-4-(4''-methylphenylethynyl)-2-fluorobenzene
1-(4'-butylphenylethynyl)-4-(4''-ethylphenylethynyl)-2-fluorobenzene
1-(4'-butylphenylethynyl)-4-(4''-propylphenylethynyl)-2-fluorobenzene
C-N point 112.6° C., N-I point 201.2° C.
1,4-bis(4'-butylphenylethynyl)-2-fluorobenzene
C-N point 91.5° C., N-I point 185.6° C.
1-(4'-butylphenylethynyl)-4-(4''-pentylphenylethynyl)-2-fluorobenzene
C-N point 78.5° C., N-I point 186.9° C.
1-(4'-butylphenylethynyl)-4-(4''-hexylphenylethynyl)-2-fluorobenzene
1-(4'-butylphenylethynyl)-4-(4''-heptylphenylethynyl)-2-fluorobenzene
1-(4'-butylphenylethynyl)-4-(4''-octylphenylethynyl)-2-fluorobenzene
1-(4'-butylphenylethynyl)-4-(4''-nonylphenylethynyl)-2-fluorobenzene
1-(4'-butylphenylethynyl)-4-(4''-decylphenylethynyl)-2-fluorobenzene
1-(4'-pentylphenylethynyl)-4-(4''-methylphenylethynyl)-2-fluorobenzene
1-(4'-pentylphenylethynyl)-4-(4''-ethylphenylethynyl)-2-fluorobenzene
1-(4'-pentylphenylethynyl)-4-(4''-propylphenylethynyl)-2-fluorobenzene
C-N point 88.3° C., N-I point 203.0° C.
1-(4'-pentylphenylethynyl)-4-(4''-butylphenylethynyl)-2-fluorobenzene
C-N point 82.4° C., N-I point 187.7° C.
1,4-bis(4'-pentylphenylethynyl)-2-fluorobenzene
C-N point 89.2° C., N-I point 189.0° C.
1-(4'-pentylphenylethynyl)-4-(4''-hexylphenylethynyl)-2-fluorobenzene
1-(4'-pentylphenylethynyl)-4-(4''-heptylphenylethynyl)-2-fluorobenzene
1-(4'-pentylphenylethynyl)-4-(4''-octylphenylethynyl)-2-fluorobenzene
1-(4'-pentylphenylethynyl)-4-(4''-nonylphenylethynyl)-2-fluorobenzene
1-(4'-pentylphenylethynyl)-4-(4''-decylphenylethynyl)-2-fluorobenzene
1-(4'-hexylphenylethynyl)-4-(4''-methylphenylethynyl)-2-fluorobenzene
1-(4'-hexylphenylethynyl)-4-(4''-ethylphenylethynyl)-2-fluorobenzene
1-(4'-hexylphenylethynyl)-4-(4''-propylphenylethynyl)-2-fluorobenzene
1-(4'-hexylphenylethynyl)-4-(4''-butylphenylethynyl)-2-fluorobenzene 1-(4'-hexylphenylethynyl)-4-(4''-pentylphenylethynyl)-2-fluorobenzene
1,4-bis(4'-hexylphenylethynyl)-2-fluorobenzene
1-(4'-hexylphenylethynyl)-4-(4''-heptylphenylethynyl)-2-fluorobenzene
1-(4'-hexylphenylethynyl)-4-(4''-octylphenylethynyl)-2-fluorobenzene
1-(4'-hexylphenylethynyl)-4-(4''-nonylphenylethynyl)-2-fluorobenzene
1-(4'-hexylphenylethynyl)-4-(4''-decylphenylethynyl)-2-fluorobenzene
1-(4'-heptylphenylethynyl)-4-(4''-methylphenylethynyl)-2-fluorobenzene
1-(4'-heptylphenylethynyl)-4-(4''-ethylphenylethynyl)-2-fluorobenzene
1-(4'-heptylphenylethynyl)-4-(4''-propylphenylethynyl)-2-fluorobenzene
1-(4'-heptylphenylethynyl)-4-(4''-butylphenylethynyl)-2-fluorobenzene
1-(4'-heptylphenylethynyl)-4-(4''-pentylphenylethynyl)-2-fluorobenzene
1-(4'-heptylphenylethynyl)-4-(4''-hexylphenylethynyl)-2-fluorobenzene
1,4-bis(4'-heptylphenylethynyl)-2-fluorobenzene
1-(4'-heptylphenylethynyl)-4-(4''-octylphenylethynyl)-2-fluorobenzene
1-(4'-heptylphenylethynyl)-4-(4''-nonylphenylethynyl)-2-fluorobenzene
1-(4'-heptylphenylethynyl)-4-(4''-decylphenylethynyl)-2-fluorobenzene
1-(4'-octylphenylethynyl)-4-(4''-methylphenylethynyl)-2-fluorobenzene
1-(4'-octylphenylethynyl)-4-(4''-ethylphenylethynyl)-2-fluorobenzene
1-(4'-octylphenylethynyl)-4-(4''-propylphenylethynyl)-2-fluorobenzene
1-(4'-octylphenylethynyl)-4-(4''-butylphenylethynyl)-2-fluorobenzene
1-(4'-octylphenylethynyl)-4-(4''-pentylphenylethynyl)-2-fluorobenzene
1-(4'-octylphenylethynyl)-4-(4''-hexylphenylethynyl)-2-fluorobenzene
1-(4'-octylphenylethynyl)-4-(4''-heptylphenylethynyl)-2-fluorobenzene
1,4-bis(4'-octylphenylethynyl)-2-fluorobenzene
1-(4'-octylphenylethynyl)-4-(4''-nonylphenylethynyl)-2-fluorobenzene
1-(4'-octylphenylethynyl)-4-(4''-decylphenylethynyl)-2-fluorobenzene
1-(4'-nonylphenylethynyl)-4-(4''-methylphenylethynyl)-2-fluorobenzene
1-(4'-nonylphenylethynyl)-4-(4''-ethylphenylethynyl)-2-fluorobenzene
1-(4'-nonylphenylethynyl)-4-(4''-propylphenylethynyl)-2-fluorobenzene
1-(4'-nonylphenylethynyl)-4-(4''-butylphenylethynyl)-2-fluorobenzene
1-(4'-nonylphenylethynyl)-4-(4''-pentylphenylethynyl)-2-fluorobenzene
1-(4'-nonylphenylethynyl)-4-(4''-hexylphenylethynyl)-2-fluorobenzene
1-(4'-nonylphenylethynyl)-4-(4''-heptylphenylethynyl)-2-fluorobenzene
1-(4'-nonylphenylethynyl)-4-(4''-octylphenylethynyl)-2-fluorobenzene
1,4-bis(4'-nonylphenylethynyl)-2-fluorobenzene
1-(4'-nonylphenylethynyl)-4-(4''-decylphenylethynyl)-2-fluorobenzene
1-(4'-decylphenylethynyl)-4-(4''-methylphenylethynyl)-2-fluorobenzene
1-(4'-decylphenylethynyl)-4-(4''-ethylphenylethynyl)-2-fluorobenzene
1-(4'-decylphenylethynyl)-4-(4''-propylphenylethynyl)-2-fluorobenzene
1-(4'-decylphenylethynyl)-4-(4''-butylphenylethynyl)-2-fluorobenzene
1-(4'-decylphenylethynyl)-4-(4''-pentylphenylethynyl)-2-fluorobenzene
1-(4'-decylphenylethynyl)-4-(4''-hexylphenylethynyl)-2-fluorobenzene
1-(4'-decylphenylethynyl)-4-(4''-heptylphenylethynyl)-2-fluorobenzene
1-(4'-decylphenylethynyl)-4-(4''-octylphenylethynyl)-2-fluorobenzene
1,4-bis(4'-decylphenylethynyl)-2-fluorobenzene
1-(4'-decylphenylethynyl)-4-(4''-nonylphenylethynyl)-2-fluorobenzene

EXAMPLE 2

Synthesis of Compound (1-b)

Preparation of 1-(4'-pentylphenylethynyl)-4-(4''-cyanophenylethynyl)-2-fluorobenzene.

Steps 1 and 2: 4-Pentylphenylacetylene was synthesized in the same manner as Steps 6 and 7 in Example 1.

Steps 3 and 4: These steps were not needed, since 4-bromo-2-fluoro-1-iodobenzene is commercially available.

Step 5: 4-Bromo-2-fluoro-1-iodobenzene (57 g) was dissolved in diethylamine (66 ml) under nitrogen atmosphere, and then bis(triphenylphosphine)palladium(II) chloride (0.5 g) and copper(I) iodide (0.5 g) were added thereto, followed by stirring. The flask was cooled to 5° C. or lower, and then 4-pentylphenylacetylene (36 g) was added dropwise thereto. After stirring at room temperature for 5 hours, the reaction solution was poured into a mixture of concentrated hydrochloric acid (40 ml) and ice (30 g). After extraction with chloroform, the resultant was washed twice with water, followed by distilling off chloroform therefrom. The residue was distilled under reduced pressure (b.p. 205° to 210° C./3 mmHg), and then recrystallized from a mixed solvent of acetone and methanol to give 4-bromo-2-fluoro-4'-pentyltolane (27 g).

Step 6: 4-Bromobenzonitrile (30 g), 3-methyl-1-butyne-3-ol (13.4 g), triphenylphosphine (0.7 g) and bis(triphenylphosphine)palladium(II) chloride (0.3 g) were dissolved in triethylamine (140 ml) under nitrogen atmosphere, and then copper(I) iodide (0.1 g) was added thereto. After stirring at room temperature for 1 hour, the reaction mixture was further stirred at 90° C. for 5 hours. The resulting precipitated crystals were filtered, and then triethylamine was distilled off therefrom, followed by extracting with chloroform. The resultant was washed twice with 10% hydrochloric acid, and further with water twice, and then chloroform was distilled off therefrom. The residue was distilled under reduced pressure (140° to 160° C./5 mmHg) to give 3-methyl-1-(4'-cyanophenyl)-1-butyne-3-ol (23.5 g).

Step 7: 3-Methyl-1-(4'-cyanophenyl)-1-butyne-3-ol (23.5 g) was dissolved in toluene (250 ml) under nitrogen atmosphere, and then sodium hydride (1.6 g) was added thereto, followed by stirring at 80° to 90° C. for 4 hours. The reaction solution was poured into water (300 ml), and then extracted with chloroform, followed by washing with water 3 times. After distilling off toluene and chloroform, the resultant was recrystallized from methanol to give 4-cyanophenylacetylene (9.9 g).

Step 8: 4-Bromo-2-fluoro-4'-pentyltolane (5.2 g), 4-cyanophenylacetylene (1.9 g), triphenylphosphine (0.06 g) and bis(triphenylphosphine)palladium(II) chloride (0.04 g) were dissolved in triethylamine (33 ml) under nitrogen atmosphere, and then copper(I) iodide (0.01 g) was added thereto, followed by refluxing for 5 hours. The reaction solution was poured into water (300 ml), and then extracted with chloroform. After washing the resultant with water twice, chloroform was distilled off therefrom. The residue was purified using silica gel-chloroform column chromatography, and then recrystallized from a mixed solvent of acetone and chloroform to give 1-(4'-pentylphenylethynyl)-4-(4''-cyanophenylethynyl)-2-fluorobenzene (2.7 g). The C-N point and the N-I point of the compound were 150.5° C. and 256.5° C., respectively.

The following compounds were synthesized in the same manner as the above method:

1-(4'-methylphenylethynyl)-4-(4''-cyanophenylethynyl)-2-fluorobenzene 1-(4'-ethylphenylethynyl)-4-(4''-cyanophenylethynyl)-2-fluorobenzene 1-(4'-propylphenylethynyl)-4-(4''-cyanophenylethynyl)-2-fluorobenzene 1-(4'-butylphenylethynyl)-4-(4''-cyanophenylethynyl)-2-fluorobenzene 1-(4'-hexylphenylethynyl)-4-(4''-cyanophenylethynyl)-2-fluorobenzene 1-(4'-heptylphenylethynyl)-4-(4''-cyanophenylethynyl)-2-fluorobenzene 1-(4'-octylphenylethynyl)-4-(4''-cyanophenylethynyl)-2-fluorobenzene 1-(4'-nonylphenylethynyl)-4-(4''-cyanophenylethynyl)-2-fluorobenzene 1-(4'-decylphenylethynyl)-4-(4''-cyanophenylethynyl)-2-fluorobenzene

EXAMPLE 3

Synthesis of Compound (1-c)

Preparation of 4-(4'-propylphenylethynyl)-1-(4''-cyanophenylethynyl)-2-fluorobenzene.

Steps 1 and 2: 4-Pentylphenylacetylene was synthesized in the same manner as Steps 6 and 7 in Example 1.

Step 3: This step was not needed, since 2-fluoro-4-iodoaniline is commercially available.

Step 4: Sodium nitrite (51.2 g) was dissolved in sulfuric acid (390 ml), and then acetic acid (454 ml) was added thereto at 10° C. or lower. The mixed solution was kept at 20° to 25° C., and 2-fluoro-4-iodoaniline (124 g) was added for 1 hour, followed by stirring for 2 hours. The reaction solution was added dropwise to a mixed solution of copper bromide (130 g) with 48% hydrobromic acid (390 ml), and stirred overnight. Then, water (1000 ml) was added to the solution, and the resulting solution was extracted with chloroform, followed by washing with water 3 times. After distilling off chloroform, the resultant was distilled under reduced pressure (b.p. 120° to 125° C./13 mmHg), and then recrystallized from methanol to give 1-bromo-2-fluoro-4-iodobenzene (114 g).

Step 5: 1-Bromo-2-fluoro-4-iodobenzene (15 g) was dissolved in diethylamine (17 ml) under nitrogen atmosphere, and then bis(triphenylphosphine) palladium(II) chloride (0.12 g) and copper(I) iodide (0.12 g) were added thereto, followed by stirring. The flask was cooled to 5° C. or lower, and then 4-propylphenylacetylene (8 g) was added dropwise thereto. After stirring at room temperature for 5 hours, the reaction solution was poured into a mixture of concentrated hydrochloric acid (10 ml) and ice (50 g). After extraction with chloroform, the resultant was washed with water twice, followed by distilling off chloroform. The residue was recrystallized from a mixed solvent of acetone and methanol to give 4-bromo-3-fluoro-4'-propyltolane (11 g).

Steps 6 and 7: 4-Cyanophenylacetylene was synthesized in the same manner as Steps 6 and 7 in Example 2.

Step 8: 4-Bromo-3-fluoro-4'-propyltolane (4.8 g), 4-cyanophenylacetylene (1.9 g), triphenyphosphine (0.06 g) and bis(triphenylphosphine)palladium(II) chloride (0.04 g) were dissolved in triethylamine (33 ml) under nitrogen atmosphere, and then copper(I) iodide (0.01 g) was added thereto, followed by refluxing for 5 hours. The reaction solution was poured into water (300 ml), and then extracted with chloroform. After washing the resultant with water twice, chloroform was distilled off therefrom. The residue was purified using silica gel-chloroform column chromatography, and then recrystallized from a mixed solvent of acetone and chloroform, to give 4-(4'-propylphenylethynyl)-1-(4''-cyanophenylethynyl)-2-fluorobenzene (3.4 g). The C-N point and the N-I point of the compound were 163.6° C. and 275.3° C., respectively.

The following compounds were synthesized in the same manner as the above method:

4-(4'-methylphenylethynyl)-1-(4''-cyanophenylethynyl)-2-fluorobenzene 4-(4'-ethylphenylethynyl)-1-(4''-cyanophenylethynyl)-2-fluorobenzene 4-(4'-butylphenylethynyl)-1-(4''-cyanophenylethynyl)-2-fluorobenzene 4-(4'-pentylphenylethynyl)-1-(4''-cyanophenylethynyl)-2-fluorobenzene 4-(4'-hexylphenylethynyl)-1-(4''-cyanophenylethynyl)-2-fluorobenzene 4-(4'-heptylphenylethynyl)-1-(4''-cyanophenylethynyl)-2-fluorobenzene 4-(4'-octylphenylethynyl)-1-(4''-cyanophenylethynyl)-2-fluorobenzene 4-(4'-nonylphenylethynyl)-1-(4''-cyanophenylethynyl)-2-fluorobenzene 4-(4'-decylphenylethynyl)-1-(4''-cyanophenylethynyl)-2-fluorobenzene

EXAMPLE 4

Synthesis of Compound (1-d)

Preparation of 5-(4'-propylphenylethynyl)-2-(4''-butylphenylethynyl)-1,3-difluorobenzene.

Steps 1 and 2: 4-Propylphenylacetylene was synthesized in the same manner as Steps 1 and 2 in Example 1.

Step 3: 2,6-Difluoroaniline (38 g) was dissolved in acetic acid (120 ml), and then pyridine (25 g) was added thereto, followed by stirring. Then, a mixture of iodine monochloride (50 g) with acetic acid (30 ml) was added dropwise thereto. After stirring at room temperature for 1 hour, the reaction solution was further stirred at 70° to 80° C. for 2 hours. Then, the reaction solution was poured into water, and the precipitated crystals were filtered, followed by washing with water. The resulting crystals were dissolved in chloroform, and then washed with water twice, further with 10% potassium hydroxide aqueous solution twice, and furthermore with water twice, followed by distilling off chloroform. The residue was distilled under reduced pressure (b.p. 120° to 130° C./20 mmHg), and then recrystallized from methanol to give 4-iodo-2,6-difluoroaniline (44 g).

Step 4: Sodium nitrite (17 g) was dissolved in sulfuric acid (130 ml), and then acetic acid (150 ml) was added thereto at 10° C. or lower. The mixed solution was kept at 20° to 25° C., and 4-iodo-2,6-difluoroaniline (44 g) was added thereto for 1 hour, followed by stirring for 2 hours. The reaction solution was added dropwise to a mixed solution of copper(I) bromide (43 g) with 48% hydrobromic acid (125 ml), and stirred overnight. Then, water (1000 ml) was added to the solution, and the resulting solution was extracted with chloroform, followed by washing with water 3 times. After distilling off chloroform, the resultant was recrystallized from methanol to give 2-bromo-1,3-difluoro-4-iodobenzene (38 g).

Step 5: 2-Bromo-1,3-difluoro-4-iodobenzene (20 g) was dissolved in diethylamine (30 ml) under nitrogen atmosphere, and then bis(triphenylphosphine)palladium(II) chloride (0.06 g) and copper(I) iodide (0.06 g) were added thereto, followed by stirring. The flask was cooled to 5° C. or lower, and then 4-propylphenylacetylene (10 g) was added dropwise thereto. After stirring at room temperature for 5 hours, the reaction solution was poured into a mixture of concentrated hydrochloric acid (15 ml) and ice (30 g). After extraction with chloroform, the resultant was washed with water twice, followed by distilling off chloroform. The residue was distilled under reduced pressure (b.p. 185° to 192° C./4 mmHg), and then recrystallized from a mixed solvent of acetone and methanol to give 4-bromo-3,5-difluoro-4'-propyltolane (12 g).

Step 6: 1-Bromo-4-butylbenzene (235 g), 3-methyl-1-butyne-3-ol (139 g), triphenylphosphine (4.8 g) and bis(triphenylphosphine)palladium(II) chloride (2.8 g) were dissolved in triethylamine (1,000 ml), and then copper(I) iodide (0.8 g) was added thereto. After stirring at room temperature for 1 hour, the reaction mixture was further stirred at 90° C. for 5 hours. The resulting precipitated crystals were filtered, and then triethylamine was distilled off therefrom, followed by extracting with chloroform. The resultant was washed with 10% hydrochloric acid twice, and further with water twice, and then chloroform was distilled off therefrom. The residue was purified using silica gel-chloroform column chromatography to give 3-methyl-1-(4'-butylphenyl)-1-butyne-3-ol (100 g).

Step 7: 3-Methyl-1-(4'-butylphenyl)-1-butyne-3-ol (100 g) was dissolved in toluene (900 ml) under nitrogen atmosphere, and then sodium hydride (60% in paraffin liquid; 5.7 g) was added thereto, followed by stirring at 60° C. for 6 hours. The reaction solution was poured into water (500 ml), and then extracted with chloroform, followed by washing with water 3 times. After distilling off toluene and chloroform, the resultant was distilled under reduced pressure (b.p. 62° to 65° C./3 mmHg) to give 4-butylphenylacetylene (63 g).

Step 8: 4-Bromo-3,5-difluoro-4'-propyltolane (5.0 g), 4-butylphenylacetylene (2.4 g), triphenylphosphine (0.06 g) and bis(triphenylphosphine)palladium(II) chloride (0.04 g) were dissolved in triethylamine (33 ml) under nitrogen atmosphere, and then copper(I) iodide (0.01 g) was added thereto, followed by refluxing for 5 hours. The reaction solution was poured into a mixture of concentrated hydrochloric acid (16 ml) and ice (30 g), and then extracted with chloroform. After washing the reaction solution with water twice, chloroform was distilled off therefrom. The residue was purified using silica gel-chloroform column chromatography, and then recrystallized from acetone to give 5-(4'-propylphenylethynyl)-2-(4''-butylphenylethynyl)-1,3-difluorobenzene (3.5 g). The C-N point and the N-I point of the compound were 120.4° C. and 181.9° C., respectively.

The following compounds were synthesized in the same manner as the above method:
5-(4'-methylphenylethynyl)-2-(4''-methylphenylethynyl)-1,3-difluorobenzene
5-(4'-methylphenylethynyl)-2-(4''-ethylphenylethynyl)-1,3-difluorobenzene
5-(4'-methylphenylethynyl)-2-(4''-propylphenylethynyl)-1,3-difluorobenzene
5-(4'-methylphenylethynyl)-2-(4''-butylphenylethynyl)-1,3-difluorobenzene
5-(4'-methylphenylethynyl)-2-(4''-pentylphenylethynyl)-1,3-difluorobenzene
5-(4'-methylphenylethynyl)-2-(4''-hexylphenylethynyl)-1,3-difluorobenzene
5-(4'-methylphenylethynyl)-2-(4''-heptylphenylethynyl)-1,3-difluorobenzene
5-(4'-methylphenylethynyl)-2-(4''-octylphenylethynyl)-1,3-difluorobenzene
5-(4'-methylphenylethynyl)-2-(4''-nonylphenylethynyl)-1,3-difluorobenzene
5-(4'-methylphenylethynyl)-2-(4''-decylphenylethynyl)-1,3-difluorobenzene
5-(4'-ethylphenylethynyl)-2-(4''-methylphenylethynyl)-1,3-difluorobenzene
5-(4'-ethylphenylethynyl)-2-(4''-ethylphenylethynyl)-1,3-difluorobenzene
5-(4'-ethylphenylethynyl)-2-(4''-propylphenylethynyl)-1,3-difluorobenzene
5-(4'-ethylphenylethynyl)-2-(4''-butylphenylethynyl)-1,3-difluorobenzene
5-(4'-ethylphenylethynyl)-2-(4''-pentylphenylethynyl)-1,3-difluorobenzene
5-(4'-ethylphenylethynyl)-2-(4''-hexylphenylethynyl)-1,3-difluorobenzene
5-(4'-ethylphenylethynyl)-2-(4''-heptylphenylethynyl)-1,3-difluorobenzene
5-(4'-ethylphenylethynyl)-2-(4''-octylphenylethynyl)-1,3-difluorobenzene
5-(4'-ethylphenylethynyl)-2-(4''-nonylphenylethynyl)-1,3-difluorobenzene
5-(4'-ethylphenylethynyl)-2-(4''-decylphenylethynyl)-1,3-difluorobenzene
5-(4'-propylphenylethynyl)-2-(4''-methylphenylethynyl)-1,3-difluorobenzene
5-(4'-propylphenylethynyl)-2-(4''-ethylphenylethynyl)-1,3-difluorobenzene
5-(4'-propylphenylethynyl)-2-(4''-propylphenylethynyl)-1,3-difluorobenzene
C-N point 155.9° C., N-I point 196.9° C.
5-(4'-propylphenylethynyl)-2-(4''-pentylphenylethynyl)-1,3-difluorobenzene
C-N point 79.6° C., N-I point 182.7° C.
5-(4'-propylphenylethynyl)-2-(4''-hexylphenylethynyl)-1,3-difluorobenzene
5-(4'-propylphenylethynyl)-2-(4''-heptylphenylethynyl)-1,3-difluorobenzene
5-(4'-propylphenylethynyl)-2-(4''-octylphenylethynyl)-1,3-difluorobenzene
5-(4'-propylphenylethynyl)-2-(4''-nonylphenylethynyl)-1,3-difluorobenzene 5-(4'-propylphenylethynyl)-2-(4''-decylphenylethynyl)-1,3-difluorobenzene 5-(4'-butylphenylethynyl)-2-(4''-methylphenylethynyl)-1,3-difluorobenzene 5-(4'-butylphenylethynyl)-2-(4''-ethylphenylethynyl)-1,3-difluorobenzene 5-(4'-butylphenylethynyl)-2-(4''-propylphenylethynyl)-1,3-difluorobenzene
C-N point 115.5° C., N-I point 180.6° C.

5-(4'-butylphenylethynyl)-2-(4''-butylphenylethynyl)-1,3-difluorobenzene
C-N point 96.2° C., N-I point 167.7° C.

5-(4'-butylphenylethynyl)-2-(4''-phentylphenylethynyl)-1,3-difluorobenzene
C-N point 78.3° C., N-I point 168.7° C.

5-(4'-butylphenylethynyl)-2-(4''-hexylphenylethynyl)-1,3-difluorobenzene 5-(4'-butylphenylethynyl)-2-(4''-heptylphenylethynyl)-1,2-difluorobenzene 5-(4'-butylphenylethynyl)-2-(4''-octylphenylethynyl)-1,3-difluorobenzene 5-(4'-butylphenylethynyl)-2-(4''-nonylphenylethynyl)-1,3-difluorobenzene 5-(4'-butylphenylethynyl)-2-(4''-decylphenylethynyl)-1,3-difluorobenzene 5-(4'-pentylphenylethynyl)-2-(4''-methylphenylethynyl)-1,3-difluorobenzene 5-(4'-pentylphenylethynyl)-2-(4''-ethylphenylethynyl)-1,3-difluorobenzene 5-(4'-pentylphenylethynyl)-2-(4''-propylphenylethynyl)-1,3-difluorobenzene 5-(4'-pentylphenylethynyl)-2-(4''-butylphenylethynyl)-1,3-difluorobenzene 5-(4'-pentylphenylethynyl)-2-(4''-pentylphenylethynyl)-1,3-difluorobenzene 5-(4'-pentylphenylethynyl)-2-(4''-hexylphenylethynyl)-1,3-difluorobenzene 5-(4'-pentylphenylethynyl)-2-(4''-heptylphenylethynyl)-1,3-difluorobenzene 5-(4'-pentylphenylethynyl)-2-(4''-octylphenylethynyl)-1,3-difluorobenzene 5-(4'-pentylphenylethynyl)-2-(4''-nonylphenylethynyl)-1,3-difluorobenzene 5-(4'-pentylphenylethynyl)-2-(4''-decylphenylethynyl)-1,3-difluorobenzene 5-(4'-hexylphenylethynyl)-2-(4''-methylphenylethynyl)-1,3-difluorobenzene 5-(4'-hexylphenylethynyl)-2-(4''-ethylphenylethynyl)-1,3-difluorobenzene 5-(4'-hexylphenylethynyl)-2-(4''-propylphenylethynyl)-1,3-difluorobenzene 5-(4'-hexylphenylethynyl)-2-(4''-butylphenylethynyl)-1,3-difluorobenzene 5-(4'-hexylphenylethynyl)-2-(4''-pentylphenylethynyl)-1,3-difluorobenzene 5-(4'-hexylphenylethynyl)-2-(4''-hexylphenylethynyl)-1,3-difluorobenzene 5-(4'-hexylphenylethynyl)-2-(4''-heptylphenylethynyl)-1,3-difluorobenzene 5-(4'-hexylphenylethynyl)-2-(4''-octylphenylethynyl)-1,3-difluorobenzene 5-(4'-hexylphenylethynyl)-2-(4''-nonylphenylethynyl)-1,3-difluorobenzene 5-(4'-hexylphenylethynyl)-2-(4''-decylphenylethynyl)-1,3-difluorobenzene 5-(4'-heptylphenylethynyl)-2-(4''-methylphenylethynyl)-1,3-difluorobenzene 5-(4'-heptylphenylethynyl)-2-(4''-ethylphenylethynyl)-1,3-difluorobenzene 5-(4'-heptylphenylethynyl)-2-(4''-propylphenylethynyl)-1,3-difluorobenzene 5-(4'-heptylphenylethynyl)-2-(4''-butylphenylethynyl)-1,3difluorobenzene 5-(4'-heptylphenylethynyl)-2-(4''-pentylphenylethynyl)-1,3-difluorobenzene 5-(4'-heptylphenylethynyl)-2-(4''-hexylphenylethynyl)-1,3-difluorobenzene 5-(4'-heptylphenylethynyl)-2-(4''-heptylphenylethynyl)-1,3-difluorobenzene 5-(4'-heptylphenylethynyl)-2-(4''-octylphenylethynyl)-1,3-difluorobenzene 5-(4'-heptylphenylethynyl)-2-(4''-nonylphenylethynyl)-1,3-difluorobenzene 5-(4'-heptylphenylethynyl)-2-(4''-decylphenylethynyl)-1,3-difluorobenzene 5-(4'-octylphenylethynyl)-2-(4''-methylphenylethynyl)-1,3-difluorobenzene 5-(4'-octylphenylethynyl)-2-(4''-ethylphenylethynyl)-1,3-difluorobenzene 5-(4'-octylphenylethynyl)-2-(4''-propylphenylethynyl)-1,3-difluorobenzene 5-(4'-octylphenylethynyl)-2-(4''-butylphenylethynyl)-1,3-difluorobenzene 5-(4'-octylphenylethynyl)-2-(4''-pentylphenylethynyl)-1,3-difluorobenzene 5-(4'-octylphenylethynyl)-2-(4''-hexylphenylethynyl)-1,3-difluorobenzene 5-(4'-octylphenylethynyl)-2-(4''-heptylphenylethynyl)-1,3-difluorobenzene 5-(4'-octylphenylethynyl)-2-(4''-octylphenylethynyl)-1,3-difluorobenzene 5-(4'-octylphenylethynyl)-2-(4''-nonylphenylethynyl)-1,3-difluorobenzene 5-(4'-octylphenylethynyl)-2-(4''-decylphenylethynyl)-1,3-difluorobenzene 5-(4'-nonylphenylethynyl)-2-(4''-methylphenylethynyl)-1,3-difluorobenzene 5-(4'-nonylphenylethynyl)-2-(4''-ethylphenylethynyl)-1,3-difluorobenzene 5-(4'-nonylphenylethynyl)-2-(4''-propylphenylethynyl)-1,3-difluorobenzene 5-(4'-nonylphenylethynyl)-2-(4''-butylphenylethynyl)-1,3-difluorobenzene 5-(4'-nonylphenylethynyl)-2-(4''-pentylphenylethynyl)-1,3-difluorobenzene 5-(4'-nonylphenylethynyl)-2-(4''-hexylphenylethynyl)-1,3-difluorobenzene 5-(4'-nonylphenyethynyl)-2-(4''-heptylphenylethynyl)-1,3-difluorobenzene 5-(4'-nonylphenylethynyl)-2-(4''-octylphenylethynyl)-1,3-difluorobenzene 5-(4'-nonylphenylethynyl)-2-(4''-nonylphenylethynyl)-1,3-difluorobenzene 5-(4'-nonylphenylethynyl)-2-(4''-decylphenylethynyl)-1,3-difluorobenzene 5-(4'-decylphenylethynyl)-2-(4''-methylphenylethynyl)-1,3-difluorobenzene 5-(4'-decylphenylethynyl)-2-(4''-ethylphenylethynyl)-1,3-difluorobenzene 5-(4'-decylphenylethynyl)-2-(4''-propylphenylethynyl)-1,3-difluorobenzene 5-(4'-decylphenylethynyl)-2-(4''-butylphenylethynyl)-1,3-difluorobenzene 5-(4'-decylphenylethynyl)-2-(4''-pentylphenylethynyl)-1,3-difluorobenzene 5-(4'-decylphenylethynyl)-2-(4"-hexylphenylethynyl)-1,3-difluorobenzene 5-(4'-decylphenylethynyl)-2-(4"-heptylphenylethynyl)-1,3-difluorobenzene 5-(4'-decylphenylethynyl)-2-(4"-octylphenylethynyl)-1,3-difluorobenzene 5-(4'-decylphenylethynyl)-2-(4"-nonylphenylethynyl)-1,3-difluorobenzene 5-(4'-decylphenylethynyl)-2-(4"-decylphenylethynyl)-1,3-difluorobenzene

EXAMPLE 5

Synthesis of Compound (1-e)

Preparation of 5-(4'-propylphenylethynyl)-2-(4"-cyanophenylethynyl)-1,3-difluorobenzene.

Steps 1 and 2: 4-Propylphenylacetylene was synthesized in the same manner as Steps 1 and 2 in Example 1.

Steps 3 and 4: 2-Bromo-1,3-difluoro-4-iodobenzene was synthesized in the same manner as Steps 3 and 4 in Example 4.

Step 5: 2-Bromo-1,3-difluoro-4-iodobenzene (20 g) was dissolved in diethylamine (30 ml) under nitrogen atmosphere, and then bis(triphenylphosphine)palladium(II) chloride (0.06 g) and copper(I) iodide (0.06 g) were added thereto, followed by stirring. The flask was cooled to 5° C. or lower, and then 4-propylphenylacetylene (10 g) was added dropwise thereto. After stirring at room temperature for 5 hours, the reaction solution was poured into a mixture of concentrated hydrochloric acid (15 ml) and ice (30 g). After extraction with chloroform, the resultant was washed twice with water, followed by distilling off chloroform. The residue was distilled under reduced pressure (b.p. 185° to 192° C./4 mmHg), and then recrystallized from a mixed solvent of acetone and methanol to give 4-bromo-3,5-difluoro-4'-propyltolane (12 g).

Steps 6 and 7: 4-Cyanophenylacetylene was synthesized in the same manner as Steps 6 and 7 in Example 2.

Step 8: 4-Bromo-3,5-difluoro-4'-propyltolane (5.0 g), 4-cyanophenylacetylene (1.9 g) triphenylphosphine (0.06 g) and bis(triphenylphosphine)palladium(II) chloride (0.04 g) were dissolved in triethylamine (33 ml) under nitrogen atmosphere, and then copper(I) iodide (0.01 g) was added thereto, followed by refluxing for 5 hours. The reaction solution was poured into water (300 ml), and then extracted with chloroform. After washing the reaction solution with water twice, chloroform was distilled off therefrom. The residue was purified using silica gel-chloroform column chromatography, and then recrystallized from a mixed solvent of acetone and chloroform to give 5-(4'-propylphenylethynyl)-2-(4"-cyanophenylethynyl)-1,3-difluorobenzene (0.7 g). The C-N point and the N-I point of the compound were 147.5° C. and 263.9° C., respectively.

The following compounds were synthesized in the same manner as the above method:

5-(4'-methylphenylethynyl)-2-(4"-cyanophenylethynyl)-1,3-difluorobenzene 5-(4'-ethylphenylethynyl)-2-(4"-cyanophenylethynyl)-1,3-difluorobenzene 5-(4'-butylphenylethynyl)-2-(4"-cyanophenylethynyl)-1,3-difluorobenzene 5-(4'-pentylphenylethynyl)-2-(4"-cyanophenylethynyl)-1,3-difluorobenzene 5-(4'-hexylphenylethynyl)-2-(4"-cyanophenylethynyl)-1,3-difluorobenzene 5-(4'-heptylphenylethynyl)-2-(4"-cyanophenylethynyl)-1,3-difluorobenzene 5-(4'-octylphenylethynyl)-2-(4"-cyanophenylethynyl)-1,3-difluorobenzene 5-(4'-nonylphenylethynyl)-2-(4"-cyanophenylethynyl)-1,3-difluorobenzene 5-(4'-decylphenylethynyl)-2-(4"-cyanophenylethynyl)-1,3-difluorobenzene

EXAMPLE 6

Synthesis of Compound (1-f)

Preparation of 1,4-bis(4'-propylphenylethynyl)-2,5-difluorobenzene.

Steps 1 and 2: 4-Propylphenylacetylene was synthesized in the same manner as Steps 1 and 2 in Example 1.

Step 3: 2,5-Difluoroaniline (38 g) was dissolved in acetic acid (120 ml), and then pyridine (25 g) was added thereto, followed by stirring. A mixed solution of iodine monochloride (50 g) with acetic acid (30 ml) was added dropwise thereto. After stirring at room temperature for 1 hour, the mixed solution was further stirred at 70° to 80° C. for 2 hours. Then, the reaction solution was poured into water, and the precipitated crystals were filtered, followed by washing with water. The resulting crystals were dissolved in chloroform, and then washed with water twice, further with 10% potassium hydroxide aqueous solution twice, and furthermore with water twice, followed by distilled off chloroform therefrom. The residue was distilled under reduced pressure (b.p. 130° to 140° C./20 mmHg), and then recrystallized from methanol, to give 4-iodo-2,5-difluoroaniline (50 g).

Step 4: Sodium nitrite (19 g) was dissolved in sulfuric acid (148 ml), and then acetic acid (170 ml) was added thereto at 10° C. or lower. The mixed solution was kept at 20° to 25° C., and 4-iodo-2,5-difluoroaniline (50 g) was added thereto for 1 hour, followed by stirring for 2 hours. The reaction solution was added dropwise to a mixed solution of copper bromide (49 g) with 48% hydrobromic acid (142 ml), and stirred overnight. Then, water (300 ml) was added to the solution, and the resulting solution was extracted with chloroform, followed by washing with water 3 times. After distilling off chloroform, the resultant was recrystallized from methanol to give 2-bromo-1,4-difluoro-4-iodobenzene (45 g).

Step 5: 2-Bromo-1,4-difluoro-4-iodobenzene (19 g) was dissolved in diethylamine (28 ml) under nitrogen atmosphere, and then bis(triphenylphosphine)palladium(II) chloride (0.06 g) and copper(I) iodide (0.06 g) were added thereto, followed by stirring. The flask was cooled to 5° C. or lower, and then 4-propylphenylacetylene (10 g) was added dropwise thereto. After stirring at room temperature for 5 hours, the reaction solution was poured into a mixture of concentrated hydrochloric acid (15 ml) and ice (30 g). After extraction with chloroform, the resultant was washed with water twice, followed by distilling off chloroform. The residue was distilled under reduced pressure (b.p. 170° to 180° C./4 mmHg) to give 4-bromo-2,5-difluoro-4'-propyltolane (16 g).

Steps 6 and 7: 4-Propylphenylacetylene was synthesized in the same manner as Steps 1 and 2 in Example 1.

Step 8: 4-Bromo-2,5-difluoro-4'-propyltolane (5.0 g), 4-propylphenylacetylene (2.1 g), triphenylphosphine (0.06 g) and bis(triphenylphosphine)palladium(II) chloride (0.04 g) were dissolved in triethylamine (33 ml) under nitrogen atmosphere, and then copper(I) iodide (0.01 g) was added thereto, followed by refluxing for 5 hours. The reaction solution was poured into a mixture of concentrated hydrochloric acid (16 ml) and ice (30 g), and then extracted with chloroform. After washing the resultant with water twice, chloroform was distilled off therefrom. The residue was purified using silica gel-chloroform column chromatography, and then recrystallized from acetone to give 1,4-bis(4'-propylphenylethynyl)-2,5-difluorobenzene (2.6 g). The C-N point and the N-I point of the compound were 153.4° C. and 197.7° C., respectively.

The following compounds were synthesized in the same manner as the above method:
1,4-bis(4'-methylphenylethynyl)-2,5-difluorobenzene
1-(4'-methylphenylethynyl)-4-(4''-ethylphenylethynyl)-2,5-difluorobenzene
1-(4'-methylphenylethynyl)-4-(4''-propylphenylethynyl)-2,5-difluorobenzene
1-(4'-methylphenylethynyl)-4-(4''-butylphenylethynyl)-2,5-difluorobenzene
1-(4'-methylphenylethynyl)-4-(4''-pentylphenylethynyl)-2,5-difluorobenzene
1-(4'-methylphenylethynyl)-4-(4''-hexylphenylethynyl)-2,5-difluorobenzene
1-(4'-methylphenylethynyl)-4-(4''-heptylphenylethynyl)-2,5-difluorobenzene
1-(4'-methylphenylethynyl)-4-(4''-octylphenylethynyl)-2,5-difluorobenzene
1-(4'-methylphenylethynyl)-4-(4''-nonylphenylethynyl)-2,5-difluorobenzene
1-(4'-methylphenylethynyl)-4-(4''-decylphenylethynyl)-2,5-difluorobenzene
1,4-bis(4'-ethylphenylethynyl)-2,5-difluorobenzene
1-(4'-ethylphenylethynyl)-4-(4''-propylphenylethynyl)-2,5-difluorobenzene
1-(4'-ethylphenylethynyl)-4-(4''-butylphenylethynyl)-2,5-difluorobenzene
1-(4'-ethylphenylethynyl)-4-(4''-pentylphenylethynyl)-2,5-difluorobenzene
1-(4'-ethylphenylethynyl)-4-(4''-hexylphenylethynyl)-2,5-difluorobenzene
1-(4'-ethylphenylethynyl)-4-(4''-heptylphenylethynyl)-2,5-difluorobenzene
1-(4'-ethylphenylethynyl)-4-(4''-octylphenylethynyl)-2,5-difluorobenzene
1-(4'-ethylphenylethynyl)-4-(4''-nonylphenylethynyl)-2,5-difluorobenzene
1-(4'-ethylphenylethynyl)-4-(4''-decylphenylethynyl)-2,5-difluorobenzene
1-(4'-propylphenylethynyl)-4-(4''-butylphenylethynyl)-2,5-difluorobenzene
C-N point 117.7° C. N-I point 183.8° C.
1-(4'-propylphenylethynyl)-4-(4''-pentylphenylethynyl)-2,5-difluorobenzene
1-(4'-propylphenylethynyl)-4-(4''-hexylphenylethynyl)-2,5-difluorobenzene
1-(4'-propylphenylethynyl)-4-(4''-heptylphenylethynyl)-2,5-difluorobenzene
1-(4'-propylphenylethynyl)-4-(4''-octylphenylethynyl)-2,5-difluorobenzene
1-(4'-propylphenylethynyl)-4-(4''-nonylphenylethynyl)-2,5-difluorobenzene
1-(4'-propylphenylethynyl)-4-(4''-decylphenylethynyl)-2,5-difluorobenzene
1,4-bis(4'-butylphenylethynyl)-2,5-difluorobenzene
C-N point 101.4° C., N-I point 169.9° C.
1-(4'-butylphenylethynyl)-4-(4''-pentylphenylethynyl)-2,5-difluorobenzene
1-(4'-butylphenylethynyl)-4-(4''-hexylphenylethynyl)-2,5-difluorobenzene
1-(4'-butylphenylethynyl)-4-(4''-heptylphenylethynyl)-2,5-difluorobenzene
1-(4'-butylphenylethynyl)-4-(4''-octylphenylethynyl)-2,5-difluorobenzene
1-(4'-butylphenylethynyl)-4-(4''-nonylphenylethynyl)-2,5-difluorobenzene
1-(4'-butylphenylethynyl)-4-(4''-decylphenylethynyl)-2,5-difluorobenzene
1,4-bis(4'-pentylphenylethynyl)-2,5-difluorobenzene
1-(4'-pentylphenylethynyl)-4-(4''-hexylphenylethynyl)-2,5-difluorobenzene
1-(4'-pentylphenylethynyl)-4-(4''-heptylphenylethynyl)-2,5-difluorobenzene
1-(4'-pentylphenylethynyl)-4-(4''-octylphenylethynyl)-2,5-difluorobenzene
1-(4'-pentylphenylethynyl)-4-(4''-nonylphenylethynyl)-2,5-difluorobenzene
1-(4'-pentylphenylethynyl)-4-(4''-decylphenylethynyl)-2,5-difluorobenzene
1,4-bis (4'-hexylphenylethynyl)-2,5-difluorobenzene
1-(4'-hexylphenylethynyl)-4-(4''-heptylphenylethynyl)-2,5-difluorobenzene
1-(4'-hexylphenylethynyl)-4-(4''-octylphenylethynyl)-2,5-difluorobenzene
1-(4'-hexylphenylethynyl)-4-(4''-nonylphenylethynyl)-2,5-difluorobenzene
1-(4'-hexylphenylethynyl)-4-(4''-decylphenylethynyl)-2,5-difluorobenzene
1,4-bis (4'-heptylphenylethynyl)-2,5-difluorobenzene
1-(4'-heptylphenylethynyl)-4-(4''-octylphenylethynyl)-2,5-difluorobenzene
1-(4'-heptylphenylethynyl)-4-(4''-nonylphenylethynyl)-2,5-difluorobenzene
1-(4'-heptylphenylethynyl)-4-(4''-decylphenylethynyl)-2,5-difluorobenzene
1,4-bis (4'-octylphenylethynyl)-2,5-difluorobenzene
1-(4'-octylphenylethynyl)-4-(4''-nonylphenylethynyl)-2,5-difluorobenzene
1-(4'-octylphenylethynyl)-4-(4''-decylphenylethynyl)-2,5-difluorobenzene
1,4-bis (4'-nonylphenylethynyl)-2,5-difluorobenzene
1-(4'-nonylphenylethynyl)-4-(4''-decylphenylethynyl)-2-fluorobenzene
1,4-bis (4'-decylphenylethynyl)-2,5-difluorobenzene

EXAMPLE 7

Synthesis of Compound (1-g)

Preparation of 5-(4'-butylphenylethynyl)-2-(4''-cyanophenylethynyl)-1,4-difluorobenzene.

Steps 1 and 2: 4-Butylphenylacetylene was synthesized in the same manner as Steps 6 and 7 in Example 4.

Steps 3 and 4: 2-Bromo-1,4-difluoro-4-iodobenzene was synthesized in the same manner as Steps 3 and 4 in Example 6.

Step 5: 2-Bromo-1,4-difluoro-4-iodobenzene (11 g) was dissolved in diethylamine (16 ml) under nitrogen atmosphere, and then bis(triphenylphosphine)palladium(II) chloride (0.03 g) and copper(I) iodide (0.03 g) were added thereto, followed by stirring. The flask was cooled to 5° C. or lower, and then 4-butylphenylacetylene (6.2 g) was added dropwise thereto. After stirring at room temperature for 5 hours, the reaction solution was poured into a mixture of concentrated hydrochloric acid (9 ml) and ice (20 g). After extraction with chloroform, the resultant was washed with water twice, followed by distilling off chloroform. The residue was distilled under reduced pressure (b.p. 170° to 180° C./5 mmHg) to give 4-bromo-2,5-difluoro-4'-butyltolane (8 g).

Steps 0 and 7: 4-Cyanophenylacetylene was synthesized in the same manner as Steps 6 and 7 in Example 2.

Step 8. 4-Bromo-2,5-difluoro-4'-butyltolane (5.2 g), 4-cyanophenylacetylene (1.9 g), triphenylphosphine (0.06 g) and bis(triphenylphosphine)palladium(II) chloride (0.04 g) were dissolved in triethylamine (33 ml) under nitrogen atmosphere, and then copper(I) iodide (0.01 g) was added thereto, followed by refluxing for 5 hours. The reaction solution was poured into water (300 ml), and then extracted with chloroform. After washing the reaction solution with water twice, chloroform was distilled off therefrom. The residue was purified using silica gel-chloroform column chromatography, and then recrystallized from a mixed solvent of acetone and chloroform to give 5-(4'-butylphenylethynyl)-2-(4''-cyanophenylethynyl)-1,4-difluorobenzene (2.9 g). The C-N point and the N-I point of the compound were 145.5° C. and 250.1° C., respectively.

The following compounds were synthesized in the same manner as the above method:

5-(4'-methylphenylethynyl)-2-(4''-cyanophenylethynyl)-1,4-difluorobenzene 5-(4'-ethylphenylethynyl)-2-(4''-cyanophenylethynyl)-1,4-difluorobenzene 5-(4'-propylphenylethynyl)-2-(4''-cyanophenylethynyl)-1,4-difluorobenzene 5-(4'-pentylphenylethynyl)-2-(4''-cyanophenylethynyl)-1,4-difluorobenzene 5-(4'-hexylphenylethynyl)-2-(4''-cyanophenylethynyl)-1,4-difluorobenzene 5-(4'-heptylphenylethynyl)-2-(4''-cyanophenylethynyl)-1,4-difluorobenzene 5-(4'-octylphenylethynyl)-2-(4''-cyanophenylethynyl)-1,4-difluorobenzene 5-(4'-nonylphenylethynyl)-2-(4''-cyanophenylethynyl)-1,4-difluorobenzene 5-(4'-decylphenylethynyl)-2-(4''-cyanophenylethynyl)-1,4-difluorobenzene

EXAMPLE 8

Liquid Crystal Composition

In order to compare the properties between the compounds of the present invention and the conventional compounds, a liquid crystal composition a containing 10% of a compound of Example 1 and comparative liquid crystal compositions b to d containing 10% of the liquid crystal compounds (i), (ii) and (v) shown in Table 1 above, respectively, were prepared in blending ratios shown in Table 2 below. ECH series liquid crystals were used as base liquid crystals.

TABLE 2

| Liquid Crystal Composition | a | b | c | d |
|---|---|---|---|---|
| 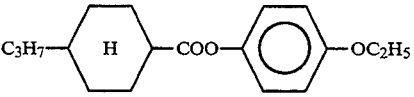 | 6.6 | 6.6 | 6.6 | 6.6 |
| 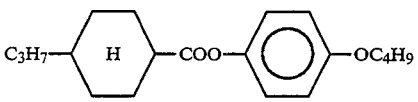 | 17.4 | 17.4 | 17.4 | 17.4 |
| 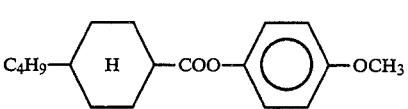 | 13.5 | 13.5 | 13.5 | 13.5 |
| 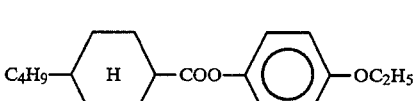 | 13.6 | 13.6 | 13.6 | 13.6 |
|  | 14.9 | 14.9 | 14.9 | 14.9 |
|  | 12.0 | 12.0 | 12.0 | 12.0 |
|  | 12.0 | 12.0 | 12.0 | 12.0 |

TABLE 2-continued

| Liquid Crystal Composition | a | b | c | d |
|---|---|---|---|---|
| 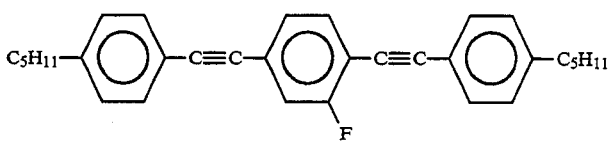 C$_5$H$_{11}$—⌬—C≡C—⌬(F)—C≡C—⌬—C$_5$H$_{11}$ | 10.0 | | | |
| 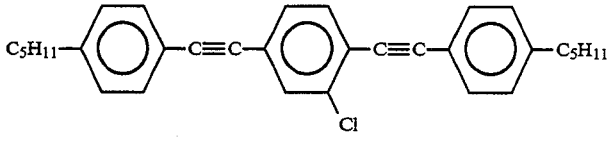 C$_5$H$_{11}$—⌬—C≡C—⌬(Cl)—C≡C—⌬—C$_5$H$_{11}$ | | 10.0 | | |
| 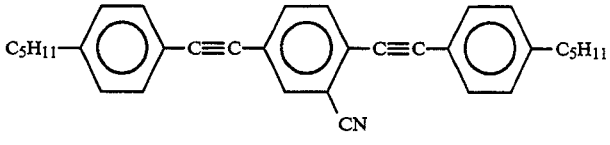 C$_5$H$_{11}$—⌬—C≡C—⌬(CN)—C≡C—⌬—C$_5$H$_{11}$ | | | 10.0 | |
| 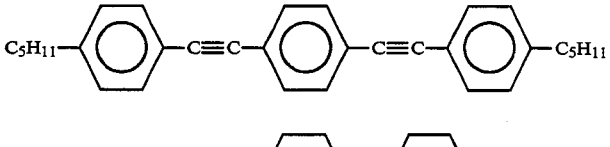 C$_5$H$_{11}$—⌬—C≡C—⌬—C≡C—⌬—C$_5$H$_{11}$ | | | | 10.0 |
|  C$_2$H$_5$—*CH(CH$_3$)—CH$_2$—⌬—⌬—CN | 0.08 | 0.08 | 0.08 | 0.08 |

The composition ratio is indicated by wt %.

In addition, for further comparison, liquid crystal compositions e to l containing 10 to 30% of the compounds of Example 1 to 7 and comparative liquid crystal compositions m to o containing 10 to 30% of conventional liquid crystal compounds currently used to increase Δn, were prepared in the blending ratios shown in Table 3 below. ECH series liquid crystals were used as the base liquid crystals. In Table 3, the composition ratio of each compound is indicated by wt %.

TABLE 3

| Liquid Crystal Composition | e | f | g | h |
|---|---|---|---|---|
|  C$_3$H$_7$—⬡(H)—COO—⌬—OC$_2$H$_5$ | 5.5 | 5.7 | 5.7 | 4.8 |
| 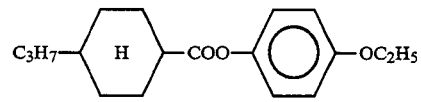 C$_3$H$_7$—⬡(H)—COO—⌬—OC$_4$H$_9$ | 14.2 | 14.7 | 14.7 | 12.6 |
| 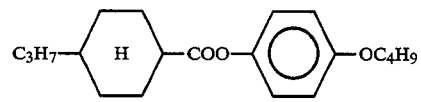 C$_4$H$_9$—⬡(H)—COO—⌬—OCH$_3$ | 11.1 | 11.5 | 11.5 | 9.9 |
| 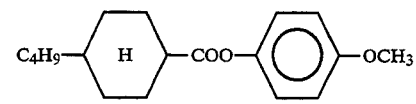 C$_4$H$_9$—⬡(H)—COO—⌬—OC$_2$H$_5$ | 11.1 | 11.5 | 11.5 | 9.9 |
| 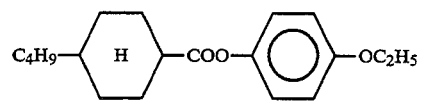 C$_5$H$_{11}$—⬡(H)—COO—⌬—OCH$_3$ | 12.1 | 12.6 | 12.6 | 10.8 |
| 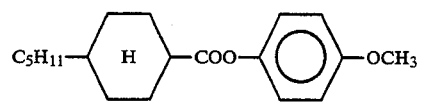 C$_2$H$_5$—⌬—COO—⌬—CN | 12.0 | 12.0 | | 10.0 |

TABLE 3-continued

| Structure | | | | |
|---|---|---|---|---|
| C₄H₉—⬡—COO—⬡—CN | 12.0 | 12.0 | | 10.0 |
| C₂H₅—⬡—⬡—CN | 6.0 | | 12.0 | 6.0 |
| C₄H₉—⬡—⬡—CN | 6.0 | | 12.0 | 6.0 |
| C₅H₁₁—⬡—C≡C—⬡(F)—C≡C—⬡—C₃H₇ | 5.0 | 10.0 | 10.0 | 10.0 |
| C₄H₉—⬡—C≡C—⬡(F)—C≡C—⬡—C₄H₉ | | | 10.0 | 5.0 |
| C₅H₁₁—⬡—C≡C—⬡(F)—C≡C—⬡—C₅H₁₁ | | | 10.0 | 5.0 |
| C₅H₁₁—⬡—C≡C—⬡(F)—C≡C—⬡—CN | 5.0 | | | |
| C₂H₅—*CH(CH₃)—CH₂—⬡—⬡—CN | 0.08 | 0.08 | 0.08 | 0.08 |

| Liquid Crystal Composition | i | j | k | l |
|---|---|---|---|---|
| C₃H₇—⬡H—COO—⬡—OC₂H₅ | 5.2 | 5.2 | 4.7 | 4.2 |
| C₃H₇—⬡H—COO—⬡—OC₄H₉ | 13.7 | 13.7 | 12.4 | 11.0 |
| C₄H₉—⬡H—COO—⬡—OCH₃ | 10.7 | 10.7 | 9.6 | 8.6 |
| C₄H₉—⬡H—COO—⬡—OC₂H₅ | 10.7 | 10.7 | 9.7 | 8.7 |

TABLE 3-continued
| Structure | | | | |
|---|---|---|---|---|
| 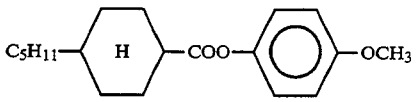 C₅H₁₁—[H]—COO—⟨⟩—OCH₃ | 11.7 | 11.7 | 10.6 | 9.5 |
| 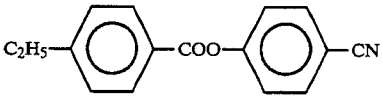 C₂H₅—⟨⟩—COO—⟨⟩—CN | 8.0 | 8.0 | 8.0 | 8.0 |
| 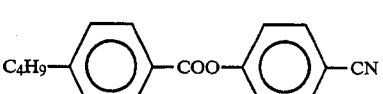 C₄H₉—⟨⟩—COO—⟨⟩—CN | 8.0 | 8.0 | 8.0 | 8.0 |
| 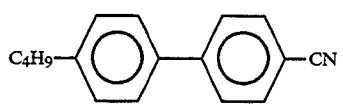 C₂H₅—⟨⟩—⟨⟩—CN | 6.0 | 6.0 | 6.0 | 6.0 |
| 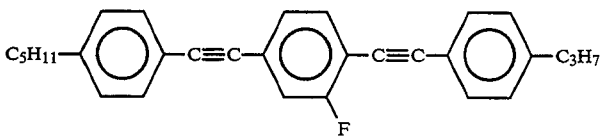 C₄H₉—⟨⟩—⟨⟩—CN | 6.0 | 6.0 | 6.0 | 6.0 |
| 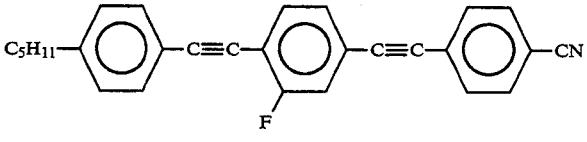 C₅H₁₁—⟨⟩—C≡C—⟨⟩(F)—C≡C—⟨⟩—C₃H₇ | | | 10.0 | 10.0 |
| 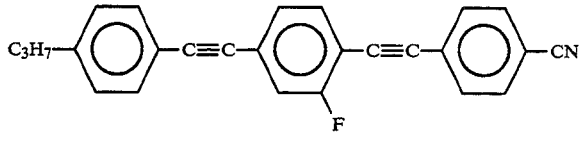 C₅H₁₁—⟨⟩—C≡C—⟨⟩(F)—C≡C—⟨⟩—CN | 5.0 | | 5.0 | 5.0 |
| 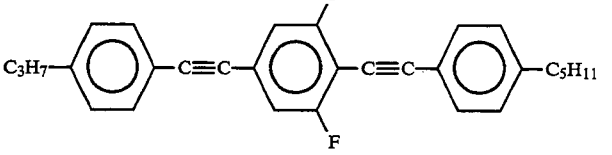 C₃H₇—⟨⟩—C≡C—⟨⟩(F)—C≡C—⟨⟩—CN | 5.0 | | | |
| 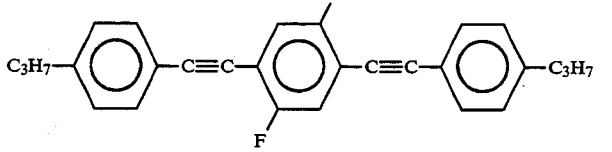 C₃H₇—⟨⟩—C≡C—⟨⟩(F,F)—C≡C—⟨⟩—C₅H₁₁ | 5.0 | 5.0 | 5.0 | 5.0 |
| 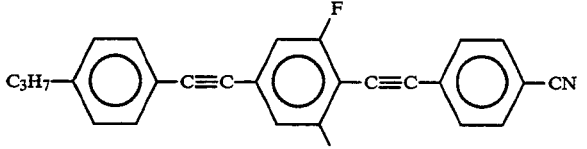 C₃H₇—⟨⟩—C≡C—⟨⟩(F,F)—C≡C—⟨⟩—C₃H₇ | 5.0 | 5.0 | 5.0 | 5.0 |
| C₃H₇—⟨⟩—C≡C—⟨⟩(F,F)—C≡C—⟨⟩—CN | | 5.0 | | 5.0 |

TABLE 3-continued

| Structure | | | |
|---|---|---|---|
| C₄H₉—⟨phenyl⟩—C≡C—⟨2,5-difluorophenyl⟩—C≡C—⟨phenyl⟩—CN | 5.0 | | |
| C₂H₅—*CH(CH₃)—CH₂—⟨phenyl⟩—⟨phenyl⟩—CN | 0.08 | 0.08 | 0.08 | 0.08 |

| Liquid Crystal Composition | m | n | o |
|---|---|---|---|
| C₃H₇—⟨H⟩—COO—⟨phenyl⟩—OC₂H₅ | 5.5 | 5.5 | 4.6 |
| C₃H₇—⟨H⟩—COO—⟨phenyl⟩—OC₄H₉ | 14.5 | 14.5 | 11.8 |
| C₄H₉—⟨H⟩—COO—⟨phenyl⟩—OCH₃ | 11.3 | 11.3 | 9.2 |
| C₄H₉—⟨H⟩—COO—⟨phenyl⟩—OC₂H₅ | 11.3 | 11.3 | 9.3 |
| C₅H₁₁—⟨H⟩—COO—⟨phenyl⟩—OCH₃ | 12.4 | 12.4 | 10.1 |
| C₃H₇—⟨pyrimidine⟩—⟨phenyl⟩—CN | 5.0 | 5.0 | 5.0 |
| C₃H₇—⟨H⟩—⟨phenyl⟩—CN | 5.0 | 10.0 | 10.0 |
| C₄H₉—⟨dioxane⟩—⟨phenyl⟩—CN | 15.0 | 10.0 | 10.0 |
| C₅H₁₁—⟨H⟩—⟨phenyl⟩—⟨phenyl⟩—C₂H₅ | 10.0 | | |
| C₃H₇—⟨H⟩—⟨phenyl⟩—COO—⟨phenyl⟩—C₅H₁₁ | | 10.0 | 15.0 |
| C₅H₁₁—⟨H⟩—⟨phenyl⟩—⟨phenyl⟩—CN | | 10.0 | 15.0 |

TABLE 3-continued

| | |
|---|---|
| C₅H₁₁—⟨phenyl⟩—⟨phenyl⟩—⟨phenyl⟩—CN | 10.0 |
| C₂H₅—*CH(CH₃)—CH₂—⟨phenyl⟩—⟨phenyl⟩—CN | 0.08  0.08  0.08 |

The N-I points and the Δn of the compositions a to o were measured. The results are shown in Table 4 below.

TABLE 4

| Liquid Crystal Composition | a | b | c | d | e |
|---|---|---|---|---|---|
| N-I point (°C.) | 70.3 | 67.8 | 65.4 | 72.6 | 65.1 |
| Δn | 0.139 | 0.135 | 0.134 | n.d. | 0.156 |
| Liquid Crystal composition | f | g | h | i | j |
| N-I point (°C.) | 81.6 | 79.4 | 77.2 | 80.5 | 78.2 |
| Δn | 0.177 | 0.187 | 0.185 | 0.195 | 0.192 |
| Liquid Crystal Composition | k | l | m | n | o |
| N-I point (°C.) | 85.6 | 93.1 | 79.2 | 80.1 | 92.6 |
| Δn | 0.209 | 0.232 | 0.119 | 0.127 | 0.128 |

Comparing liquid crystal composition a with the comparative liquid crystal compositions b to d, the N-I point of composition a is higher than those of compositions b and c. On the other hand, composition d precipitated crystals at room temperature, and consequently its Δn was impossible to measure. Accordingly, it is proved that the liquid crystal composition a containing a compound of the present invention exhibits a wider liquid crystal temperature range than the comparative liquid crystal compositions b to d containing the conventional compounds shown in Table 1.

Next, the liquid crystal compositions e to l containing the compounds of the invention are compared with the comparative liquid crystal compositions m to o containing the conventional compounds. As a result, it is proved that the Δn of the liquid crystal compositions e to l are larger than those of the comparative liquid crystal compositions m to o by 0.03 to 0.11.

EXAMPLE 9

Liquid Crystal Display Device

As shown in FIG. 1, electrodes 3 consisting of the transparent electrode membranes (e.g., ITO membrane) were formed on glass substrates 1 and 2, and then coated with the alignment membranes consisting of, for example, polyimide. Next, orientation control layers 4 were formed thereon by rubbing. Subsequently, the resulting pair of glass substrates 1 and 2 were placed opposingly through sealing material 6, and then the liquid crystal compositions a to o prepared in Example 8 were injected between the glass substrates, respectively, followed by pasting a deflecting plate outside of substrate 1 and a reflection-type deflecting plate outside of substrate 2, to give the TN mode-liquid crystal display panels A to O. The cell gap d of the liquid crystal display panels A to C were defined at 9.0 μm, and the cell gap d of the liquid crystal display panels E to O were defined so that each Δn·d value was in the range of about 1.25 to 1.35.

For each liquid crystal display cell thus obtained, the threshold voltage (hereinafter referred to as Vth), the visual angle dependency of voltage-light transmittance (hereinafter referred to as α), the rapidity (hereinafter referred to as β), the rise time (hereinafter referred to as Tr) and the drop time (i.e., the fall time; hereinafter referred to as Td), were measured according to the reflection-type measuring using the alternating current static drive. Each value of α, β and Vth was determined according to the following equations:

$$\alpha = \frac{V10(\theta = 80°, T = 25° C.)}{V10(\theta = 50°, T = 25° C.)}$$

$$\beta = \frac{V10(\theta = 80°, T = 25° C.)}{V90(\theta = 80°, T = 25° C.)}$$

$$Vth = V10$$

θ: the angle of incident light against the cell (the vertical direction against the panel as defined as 90°);

V10, V90: the voltage values at 10% and 90% of transmittance, respectively.

Tr indicates the time required to decrease the transmittance to 10% when the voltage was ON (the applied voltage was V90 (θ=80°)). Td indicates the time required for the transmittance to recover to 90% when the voltage was OFF (the applied voltage was V10 (θ80°)).

The results are shown in Table 5 below.

TABLE 5

| | Liquid Crystal Panel | | | | |
|---|---|---|---|---|---|
| | A | B | C | D | E |
| | Liquid Crystal Composition | | | | |
| | a | b | c | d | e |
| Cell Thickness (μm) | 9.0 | 9.0 | 9.0 | — | 8.0 |
| Δn · d | 1.26 | 1.22 | 1.21 | — | 1.25 |
| Vth (V) | 1.621 | 1.690 | 1.583 | — | 1.347 |
| α | 1.170 | 1.164 | 1.161 | — | 1.190 |
| β | 1.247 | 1.264 | 1.266 | — | 1.280 |
| Tr (ms) | 134 | 129 | 144 | — | 100 |
| Td (ms) | 212 | 183 | 210 | — | 132 |
| Tr + Td (ms) | 346 | 312 | 354 | — | 232 |

| | Liquid Crystal Panel | | | | |
|---|---|---|---|---|---|
| | F | G | H | I | J |
| | Liquid Crystal Composition | | | | |
| | f | g | h | i | j |
| Cell Thickness (μm) | 7.0 | 7.0 | 7.0 | 7.0 | 7.0 |
| Δn · d | 1.24 | 1.31 | 1.30 | 1.37 | 1.34 |
| Vth (V) | 1.633 | 1.995 | 1.519 | 1.516 | 1.488 |
| α | 1.163 | 1.149 | 1.180 | 1.186 | 1.189 |
| β | 1.264 | 1.247 | 1.270 | 1.278 | 1.278 |
| Tr (ms) | 79 | 65 | 71 | 73 | 71 |
| Td (ms) | 109 | 92 | 96 | 90 | 107 |
| Tr + Td (ms) | 188 | 157 | 167 | 163 | 178 |

| Liquid Crystal Panel |
|---|

TABLE 5-continued

| | K | L | M | N | O |
|---|---|---|---|---|---|
| | \multicolumn{5}{c}{Liquid Crystal Composition} | | | | |
| | k | l | m | n | o |
| Cell Thickness (μm) | 6.0 | 6.0 | 10.0 | 7.0 | 7.0 |
| Δn · d | 1.25 | 1.39 | 1.19 | 1.37 | 1.34 |
| Vth (V) | 1.637 | 1.611 | 1.645 | 1.516 | 1.488 |
| α | 1.189 | 1.194 | 1.170 | 1.186 | 1.189 |
| β | 1.270 | 1.280 | 1.259 | 1.278 | 1.278 |
| Tr (ms) | 54 | 55 | 128 | 139 | 141 |
| Td (ms) | 81 | 90 | 189 | 191 | 196 |
| Tr + Td (ms) | 135 | 145 | 317 | 330 | 337 |

Comparing the liquid crystal panel A using the liquid crystal composition containing the liquid crystal compound of the invention with the comparative liquid crystal panels B and D using the liquid crystal compositions containing the conventional liquid crystal compounds shown in Table 1, it is proved that the liquid crystal panel A has a smaller β value than the comparative liquid crystal panels B and D. Accordingly, the liquid crystal panel A can be driven by high time-sharing addressing in the TN mode display.

Furthermore, comparing the liquid crystal panels E to L which use the liquid crystal compositions containing the liquid crystal compounds of the present invention with the comparative liquid crystal panels M to O which use the liquid crystal compositions containing the conventional liquid crystal compounds, it is proved that the liquid crystal panels E to L have smaller Tr+Td values than the comparative liquid crystal panels M to O by 50 to 150 ms.

On the other hand, when the STN mode liquid crystal display cell was used instead of the TN mode liquid crystal display cell used in above Examples, similar results were obtained.

As mentioned above, the compounds of the present invention show excellent compatibility with other liquid crystal compounds. Consequently, the compounds make the practical temperature range wider and increase the Δn value when blended with general liquid crystal mixtures.

Accordingly, by using the liquid crystal compositions containing the liquid crystal compounds of the present invention, a liquid crystal display device exhibiting a wide practical temperature range and a high-speed response can be prepared.

The compounds according to the present invention are extremely useful as basic components of liquid crystal compositions used in the STN mode display system, which is the main system currently used.

What is claimed is:

1. A tolane derivative represented by the following formula:

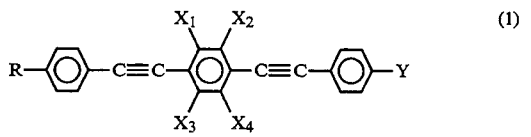

wherein R represents a straight-chain alkyl group having 1 to 10 carbon atoms, each of $X_1$, $X_2$, $X_3$ and $X_4$ represents a fluorine atom or a hydrogen atom wherein at least one X represents a fluorine atom, and Y represents a nitrile group or a straight-chain alkyl group having 1 to 10 carbon atoms.

2. A tolane derivative according to claim 1 represented by the following general formula:

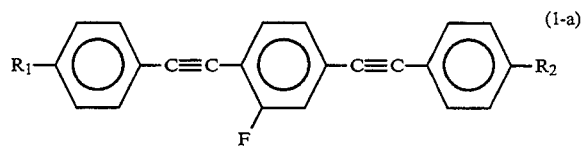

wherein each of R1 and R2 represents a straight-chain alkyl group having 1 to 10 carbon atoms.

3. A tolane derivative according to claim 1 represented by the following general formula:

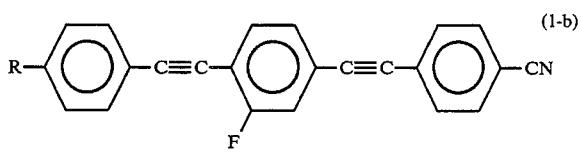

wherein R represents a straight-chain alkyl group having 1 to 10 carbon atoms.

4. A tolane derivative according to claim 1 represented by the following general formula:

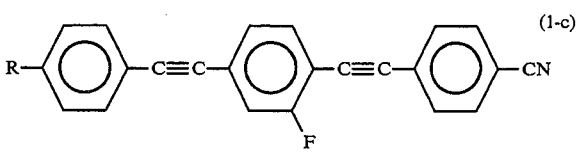

wherein R represents a straight-chain alkyl group having 1 to 10 carbon atoms.

5. A tolane derivative according to claim 1 represented by the following general formula:

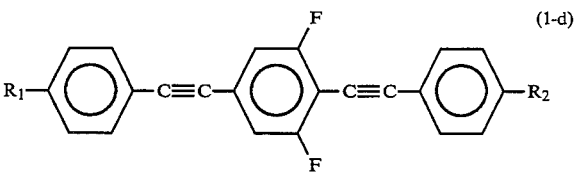

wherein each of R1 and R2 represents a straight-chain alkyl group having 1 to 10 carbon atoms.

6. A tolane derivative according to claim 1 represented by the following general formula:

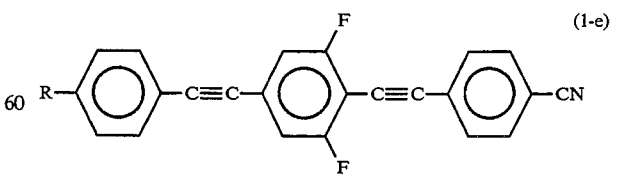

wherein R represents a straight-chain alkyl group having 1 to 10 carbon atoms.

7. A tolane derivative according to claim 1 represented by the following general formula:

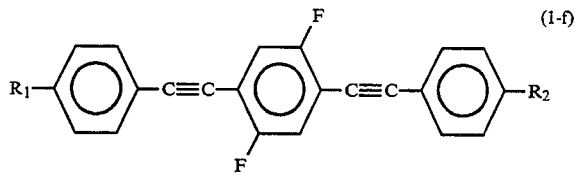

wherein each of R1 and R2 represents a straight-chain alkyl group having 1 to 10 carbon atoms.

8. A tolane derivative according to claim 1 represented by the following general formula:

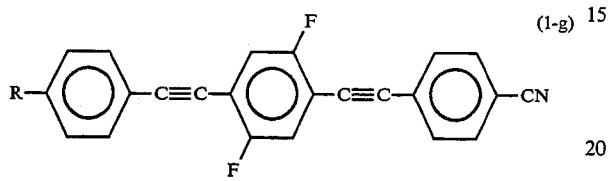

wherein R represents a straight-chain alkyl group, having 1 to 10 carbon atoms.

9. A liquid crystal composition containing at least one tolane derivative represented by the following general formula:

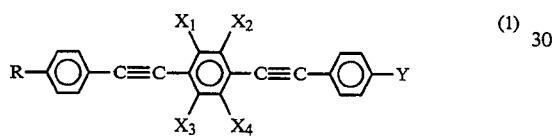

wherein R represents a straight-chain alkyl group having 1 to 10 carbon atoms, each of $X_1$, $X_2$, $X_3$ and $X_4$ represents a fluorine atom or a hydrogen atom wherein at least one X represents a fluorine atom, and Y represents a nitrile group or a straight-chain alkyl group having 1 to 10 carbon atoms.

10. A liquid crystal composition according to claim 9, which contains:

5 to 50 wt % of at least one tolane derivative represented by the following general formula:

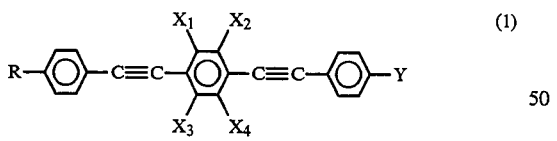

wherein R represents a straight-chain alkyl group having 1 to 10 carbon atoms, each of $X_1$, $X_2$, $X_3$ and $X_4$ represents a fluorine atom or a hydrogen atom wherein at least one X represents a fluorine atom, and Y represents a nitrile group or a straight-chain alkyl group having 1 to 10 carbon atoms; and 30 to 80 wt % of at least one cyclohexanecarboxylic acid phenyl ester derivative represented by the following general formula:

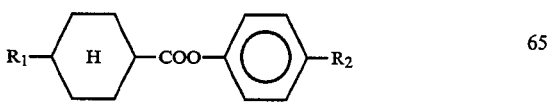

wherein each of R1 and R2 represents a straight-chain alkyl group having 1 to 10 carbon atoms, and the cyclohexane ring is trans configuration.

11. A liquid crystal composition according to claim 9, which contains:

10 to 35 wt % of at least one tolane derivative represented by the following general formula:

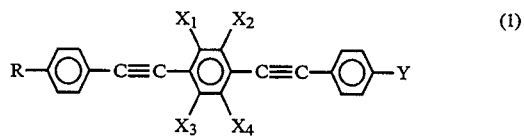

wherein R represents a straight-chain alkyl group having 1 to 10 carbon atoms, each of $X_1$, $X_2$, $X_3$ and $X_4$ represents a fluorine atom or a hydrogen atom wherein at least one X represents a fluorine atom, and Y represents a nitrile group or a straight-chain alkyl group having 1 to 10 carbon atoms;

40 to 70 wt % of at least one cyclohexanecarboxylic acid phenyl ester derivative series represented by the following general formula:

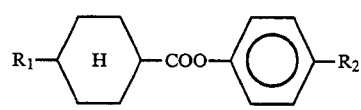

wherein each of R1 and R2 represents a straight-chain alkyl group having 1 to 10 carbon atoms and the cyclohexane ring is trans configuration; and 10 to 50 wt % of at least one compound exhibiting a positive dielectrical anisotropy represented by the following general formulae:

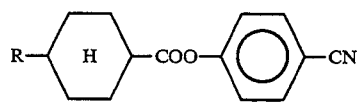

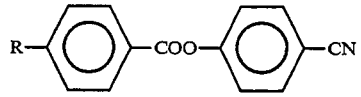

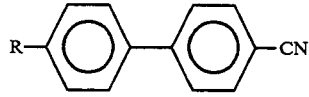

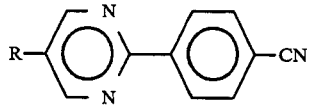

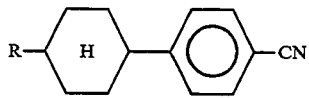

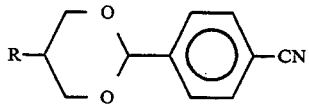

wherein R represents a straight-chain alkyl group having 1 to 10 carbon atoms and the cyclohexane ring is trans configuration.

12. A liquid crystal display device comprising a liquid crystal composition containing a tolane derivative, said liquid crystal composition containing at least one tolane derivative represented by the following general formula:

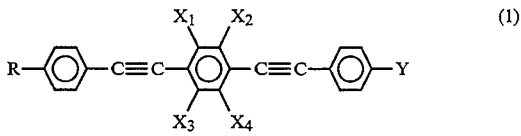

wherein R represents a straight-chain alkyl group having 1 to 10 carbon atoms, each of $X_1$, $X_2$, $X_3$ and $X_4$ represents a fluorine atom or a hydrogen atom wherein at least one X represents a fluorine atom, and Y represents a nitrile group or a straight-chain alkyl group having 1 to 10 carbon atoms.

* * * * *